US009637522B2

(12) United States Patent
Lu et al.

(10) Patent No.: US 9,637,522 B2
(45) Date of Patent: May 2, 2017

(54) INFLUENZA VACCINE CONSTRUCTS

(71) Applicant: The Board of Trustees of the Leland Stanford Junior University, Palo Alto, CA (US)

(72) Inventors: Yuan Lu, Palo Alto, CA (US); James R. Swartz, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/401,758

(22) PCT Filed: May 23, 2013

(86) PCT No.: PCT/US2013/042498
§ 371 (c)(1),
(2) Date: Nov. 17, 2014

(87) PCT Pub. No.: WO2013/177444
PCT Pub. Date: Nov. 28, 2013

(65) Prior Publication Data
US 2015/0132331 A1    May 14, 2015

Related U.S. Application Data

(60) Provisional application No. 61/650,933, filed on May 23, 2012.

(51) Int. Cl.
C07K 14/005    (2006.01)
C12N 7/00      (2006.01)
A61K 39/12     (2006.01)
C07K 14/00     (2006.01)
A61K 39/00     (2006.01)

(52) U.S. Cl.
CPC ............ *C07K 14/005* (2013.01); *A61K 39/12* (2013.01); *C07K 14/00* (2013.01); *C12N 7/00* (2013.01); *A61K 39/00* (2013.01); *A61K 2039/5258* (2013.01); *A61K 2039/6075* (2013.01); *A61K 2039/64* (2013.01); *C07K 2319/00* (2013.01); *C07K 2319/42* (2013.01); *C07K 2319/50* (2013.01); *C07K 2319/70* (2013.01); *C12N 2760/16134* (2013.01)

(58) Field of Classification Search
CPC .............. C07K 14/005; C07K 2317/76; C07K 16/1018; A61K 39/12; A61K 2039/505
See application file for complete search history.

(56) References Cited

U.S. PATENT DOCUMENTS

| 7,939,083 | B2 | 5/2011 | Dey et al. | |
|---|---|---|---|---|
| 2009/0208531 | A1* | 8/2009 | Nabel | A61K 39/145 424/209.1 |
| 2010/0014972 | A1 | 1/2010 | Steffensen | |
| 2010/0093024 | A1 | 4/2010 | Goerke et al. | |
| 2010/0167981 | A1 | 7/2010 | Bundy et al. | |
| 2010/0168402 | A1* | 7/2010 | Bundy | C07K 14/005 530/402 |
| 2010/0297174 | A1 | 11/2010 | Garcia-sastre et al. | |

FOREIGN PATENT DOCUMENTS

WO    2007/100584    9/2007

OTHER PUBLICATIONS

Khurana et al. "Bacterial HA1 Vaccine Against Pandemic H5N1 Influenza Virus: Evidence of Oligomerization, Hemagglutination, and Cross-Protective immunity in ferrels", 2011, Journal of Virology, 85:1246-1256.*
Khurana, S. et al., Bacterial HA1 Vaccine Against Pandemic H5N1 Influenza Virus: Evidence of Oligomerization, Hemugglatination, and Cross-Protective Immunity in Ferrets, Journal of Virology, Feb. 2011, vol. 85, No. 3, pp. 1246-1256.
Dawood, F. et al., Emergence of a Novel Swine-Origin Influenza A (H1N1) Virus in Humans, New England Journal of Medicine, Jun. 18, 2009, vol. 360, No. 25, pp. 2605-2615.

* cited by examiner

*Primary Examiner* — Shanon A Foley
*Assistant Examiner* — Myron Hill
(74) *Attorney, Agent, or Firm* — Pamela J. Sherwood; Bozicevic, Field & Francis LLP

(57) ABSTRACT

Vaccine compositions and methods of producing and using the same are provided, which compositions comprise a modified HA stem domain in a trimeric configuration.

12 Claims, 19 Drawing Sheets

Dissolving 1 ml CFPS products

↓

Centrifuge (14,000rpm for 15min) and discard the supernatant

↓

Wash inclusion body pellets 3 times with Washing Buffer I and 3 times with Washing Buffer II

↓

Dissolve washed inclusion bodies in Denaturing Washing Buffer by adding 5 mM DTT and votex-shaking

↓

Centrifuge (14,000rpm for 15min) and discard still insoluble fragments

Purification

Load 1 ml of denatured protein solution on Ni-NTA column

↓

Wash the column with 5 column volumes of Denaturing Washing Buffer

↓

Elute the column with 5 column volumes of Denaturing Elution Buffer

↓

Examine the purity by SDS-PAGE

↓

Dialyze against Denaturing Buffer for 4hrs at RT, twice

Refolding

Dilute 10X rapidly in Refolding Buffer

↓

Place in anaerobic glove box for 1 min and sealing the tube using Parafilm

↓

Incubate the tube at 4°C for 48hrs

↓

Dialyze against Refolding Buffer for 24hrs at 4°C

↓

Dialyze against final Dialysis Buffer for 24hrs at 4°C

FIGURE 19

| Fragments | Theoretical isoelectric point | | | | |
|---|---|---|---|---|---|
| | Wild-type | I69T+I72E +I74T+C77T | F164D | L174D | F164D +L174D |
| Stem-HA1-Fragment1 | 8.85 | 8.60 | ---- | ---- | ---- |
| Stem-HA2-Fragment1 | 8.60 | ---- | 6.75 | 6.75 | 5.38 |

FIGURE 20

SEQUENCE LISTING

<160> NUMBER OF SEQ ID NOS: 18

<210> SEQ ID NO 1
<211> LENGTH: 566
<212> TYPE: PRT
<213> ORGANISM: Artificial sequence
<220> FEATURE:
<223> OTHER INFORMATION: Synthetic amino acid sequence

<400> SEQUENCE: 1

```
Met Lys Ala Ile Leu Val Val Met Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350
```

```
Phe Ile Glu Gly Gly Trp Thr Gly Met Val Asp Gly Trp Tyr Gly Tyr
                355                 360                 365

His His Gln Asn Glu Gln Gly Ser Gly Tyr Ala Ala Asp Leu Lys Ser
        370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
        450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
        530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 2
<211> LENGTH: 504
<212> TYPE: PRT
<213> ORGANISM: Influenza A virus (A/California/05/2009(H1N1))

<400> SEQUENCE: 2

Met Asp Thr Leu Cys Ile Gly Tyr His Ala Asn Asn Ser Thr Asp Thr
1               5                   10                  15

Val Asp Thr Val Leu Glu Lys Asn Val Thr Val Thr His Ser Val Asn
                20                  25                  30

Leu Leu Glu Asp Lys His Asn Gly Lys Leu Cys Lys Leu Arg Gly Val
            35                  40                  45

Ala Pro Leu His Leu Gly Lys Cys Asn Ile Ala Gly Trp Ile Leu Gly
        50                  55                  60

Asn Pro Glu Cys Glu Ser Leu Ser Thr Ala Ser Ser Trp Ser Tyr Ile
65                  70                  75                  80

Val Glu Thr Ser Ser Ser Asp Asn Gly Thr Cys Tyr Pro Gly Asp Phe
                85                  90                  95

Ile Asp Tyr Glu Glu Leu Arg Glu Gln Leu Ser Ser Val Ser Ser Phe
                100                 105                 110

Glu Arg Phe Glu Ile Phe Pro Lys Thr Ser Ser Trp Pro Asn His Asp
            115                 120                 125

Ser Asn Lys Gly Val Thr Ala Ala Cys Pro His Ala Gly Ala Lys Ser
        130                 135                 140

Phe Tyr Lys Asn Leu Ile Trp Leu Val Lys Lys Gly Asn Ser Tyr Pro
145                 150                 155                 160
```

```
Lys Leu Ser Lys Ser Tyr Ile Asn Asp Lys Gly Lys Glu Val Leu Val
                165                 170                 175

Leu Trp Gly Ile His His Pro Ser Thr Ser Ala Asp Gln Gln Ser Leu
            180                 185                 190

Tyr Gln Asn Ala Asp Ala Tyr Val Phe Val Gly Ser Ser Arg Tyr Ser
        195                 200                 205

Lys Lys Phe Lys Pro Glu Ile Ala Ile Arg Pro Lys Val Arg Asp Gln
    210                 215                 220

Glu Gly Arg Met Asn Tyr Tyr Trp Thr Leu Val Glu Pro Gly Asp Lys
225                 230                 235                 240

Ile Thr Phe Glu Ala Thr Gly Asn Leu Val Val Pro Arg Tyr Ala Phe
                245                 250                 255

Ala Met Glu Arg Asn Ala Gly Ser Gly Ile Ile Ile Ser Asp Thr Pro
            260                 265                 270

Val His Asp Cys Asn Thr Thr Cys Gln Thr Pro Lys Gly Ala Ile Asn
        275                 280                 285

Thr Ser Leu Pro Phe Gln Asn Ile His Pro Ile Thr Ile Gly Lys Cys
    290                 295                 300

Pro Lys Tyr Val Lys Ser Thr Lys Leu Arg Leu Ala Thr Gly Leu Arg
305                 310                 315                 320

Asn Val Pro Ser Ile Gln Ser Arg Gly Leu Phe Gly Ala Ile Ala Gly
                325                 330                 335

Phe Ile Glu Gly Gly Trp Thr Gly Met Val Asp Gly Trp Tyr Gly Tyr
            340                 345                 350

His His Gln Asn Glu Gln Gly Ser Gly Tyr Ala Ala Asp Leu Lys Ser
        355                 360                 365

Thr Gln Asn Ala Ile Asp Glu Ile Thr Asn Lys Val Asn Ser Val Ile
    370                 375                 380

Glu Lys Met Asn Thr Gln Phe Thr Ala Val Gly Lys Glu Phe Asn His
385                 390                 395                 400

Leu Glu Lys Arg Ile Glu Asn Leu Asn Lys Lys Val Asp Asp Gly Phe
                405                 410                 415

Leu Asp Ile Trp Thr Tyr Asn Ala Glu Leu Leu Val Leu Leu Glu Asn
            420                 425                 430

Glu Arg Thr Leu Asp Tyr His Asp Ser Asn Val Lys Asn Leu Tyr Glu
        435                 440                 445

Lys Val Arg Ser Gln Leu Lys Asn Asn Ala Lys Glu Ile Gly Asn Gly
    450                 455                 460

Cys Phe Glu Phe Tyr His Lys Cys Asp Asn Thr Cys Met Glu Ser Val
465                 470                 475                 480

Lys Asn Gly Thr Tyr Asp Tyr Pro Lys Tyr Ser Glu Glu Ala Lys Leu
                485                 490                 495

Asn Arg Glu Glu Ile Asp Gly Val
            500

<210> SEQ ID NO 3
<211> LENGTH: 503
<212> TYPE: PRT
<213> ORGANISM: Influenza A virus (A/Viet Nam/1203/2004(H5N1))

<400> SEQUENCE: 3

Met Asp Gln Ile Cys Ile Gly Tyr His Ala Asn Asn Ser Thr Glu Gln
1               5                   10                  15

Val Asp Thr Ile Met Glu Lys Asn Val Thr Val Thr His Ala Gln Asp
            20                  25                  30
```

```
Ile Leu Glu Lys Lys His Asn Gly Lys Leu Cys Asp Leu Asp Gly Val
            35                  40                  45
Lys Pro Leu Ile Leu Arg Asp Cys Ser Val Ala Gly Trp Leu Leu Gly
 50                  55                  60
Asn Pro Met Cys Asp Glu Phe Ile Asn Val Pro Glu Trp Ser Tyr Ile
 65                  70                  75                  80
Val Glu Lys Ala Asn Pro Val Asn Asp Leu Cys Tyr Pro Gly Asp Phe
                 85                  90                  95
Asn Asp Tyr Glu Glu Leu Lys His Leu Leu Ser Arg Ile Asn His Phe
                100                 105                 110
Glu Lys Ile Gln Ile Ile Pro Lys Ser Ser Trp Ser Ser His Glu Ala
            115                 120                 125
Ser Leu Gly Val Ser Ser Ala Cys Pro Tyr Gln Gly Lys Ser Ser Phe
            130                 135                 140
Phe Arg Asn Val Val Trp Leu Ile Asn Lys Asn Ser Thr Tyr Pro Thr
145                 150                 155                 160
Ile Lys Arg Ser Tyr Asn Asn Thr Asn Gln Glu Asp Leu Leu Val Leu
                165                 170                 175
Trp Gly Ile His His Pro Asn Asp Ala Ala Glu Gln Thr Lys Leu Tyr
            180                 185                 190
Gln Asn Pro Thr Thr Tyr Ile Ser Val Gly Thr Ser Thr Leu Asn Gln
            195                 200                 205
Arg Leu Val Pro Arg Ile Ala Thr Arg Ser Lys Val Asn Gly Gln Ser
210                 215                 220
Gly Arg Met Glu Phe Phe Trp Thr Ile Leu Lys Pro Asn Asp Ala Ile
225                 230                 235                 240
Asn Phe Glu Ser Asn Gly Asn Phe Ile Ala Pro Glu Tyr Ala Tyr Lys
                245                 250                 255
Ile Val Lys Lys Gly Asp Ser Thr Ile Met Lys Ser Glu Leu Glu Tyr
            260                 265                 270
Gly Asn Cys Asn Thr Lys Cys Gln Thr Pro Met Gly Ala Ile Asn Ser
            275                 280                 285
Ser Met Pro Phe His Asn Ile His Pro Leu Thr Ile Gly Glu Cys Pro
            290                 295                 300
Lys Tyr Val Lys Ser Asn Arg Leu Val Leu Ala Thr Gly Leu Arg Asn
305                 310                 315                 320
Ser Pro Gln Arg Glu Thr Arg Gly Leu Phe Gly Ala Ile Ala Gly Phe
                325                 330                 335
Ile Glu Gly Gly Trp Gln Gly Met Val Asp Gly Trp Tyr Gly Tyr His
            340                 345                 350
His Ser Asn Glu Gln Gly Ser Gly Tyr Ala Ala Asp Lys Glu Ser Thr
            355                 360                 365
Gln Lys Ala Ile Asp Gly Val Thr Asn Lys Val Asn Ser Ile Ile Asp
            370                 375                 380
Lys Met Asn Thr Gln Phe Glu Ala Val Gly Arg Glu Phe Asn Asn Leu
385                 390                 395                 400
Glu Arg Arg Ile Glu Asn Leu Asn Lys Lys Met Glu Asp Gly Phe Leu
                405                 410                 415
Asp Val Trp Thr Tyr Asn Ala Glu Leu Leu Val Leu Met Glu Asn Glu
            420                 425                 430
Arg Thr Leu Asp Phe His Asp Ser Asn Val Lys Asn Leu Tyr Asp Lys
            435                 440                 445
```

```
Val Arg Leu Gln Leu Arg Asp Asn Ala Lys Glu Leu Gly Asn Gly Cys
    450                 455                 460

Phe Glu Phe Tyr His Lys Cys Asp Asn Glu Cys Met Glu Ser Val Arg
465                 470                 475                 480

Asn Gly Thr Tyr Asp Tyr Pro Gln Tyr Ser Glu Glu Ala Arg Leu Lys
                485                 490                 495

Arg Glu Glu Ile Ser Gly Val
            500

<210> SEQ ID NO 4
<211> LENGTH: 505
<212> TYPE: PRT
<213> ORGANISM: Influenza A virus (A/Hong Kong/1/1968(H3N2))
<220> FEATURE:
<221> NAME/KEY: misc_feature
<222> LOCATION: (145)..(145)
<223> OTHER INFORMATION: Xaa can be any naturally occurring amino acid

<400> SEQUENCE: 4

Met Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
    50                  55                  60

Thr Leu Ile Asp Ala Leu Leu Gly Asp Pro His Cys Asp Val Phe Gln
65                  70                  75                  80

Asn Glu Thr Trp Asp Leu Phe Val Glu Arg Ser Lys Ala Phe Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Thr Glu Gly Phe Thr Trp Thr
        115                 120                 125

Gly Val Thr Gln Asn Gly Gly Ser Asn Ala Cys Lys Arg Gly Pro Gly
    130                 135                 140

Xaa Gly Phe Phe Ser Arg Leu Asn Trp Leu Thr Lys Ser Gly Ser Thr
145                 150                 155                 160

Tyr Pro Val Leu Asn Val Thr Met Pro Asn Asn Asp Asn Phe Asp Lys
                165                 170                 175

Leu Tyr Ile Trp Gly Val His His Pro Ser Thr Asn Gln Glu Gln Thr
            180                 185                 190

Ser Leu Tyr Val Gln Ala Ser Gly Arg Val Thr Val Ser Thr Arg Arg
        195                 200                 205

Ser Gln Gln Thr Ile Ile Pro Asn Ile Gly Ser Arg Pro Trp Val Arg
    210                 215                 220

Gly Met Ser Ser Arg Ile Ser Ile Tyr Trp Thr Ile Val Lys Pro Gly
225                 230                 235                 240

Asp Val Leu Val Ile Asn Ser Asn Gly Asn Leu Ile Ala Pro Arg Gly
                245                 250                 255

Tyr Phe Lys Met Arg Thr Gly Lys Ser Ser Ile Met Arg Ser Asp Ala
            260                 265                 270

Pro Ile Asp Thr Cys Ile Ser Glu Cys Ile Thr Pro Asn Gly Ser Ile
        275                 280                 285
```

```
Pro Asn Asp Lys Pro Phe Gln Asn Val Asn Lys Ile Thr Tyr Gly Ala
    290                 295                 300

Cys Pro Lys Tyr Val Lys Gln Asn Thr Leu Lys Leu Ala Thr Gly Met
305                 310                 315                 320

Arg Asn Val Pro Glu Lys Gln Thr Arg Gly Leu Phe Gly Ala Ile Ala
                325                 330                 335

Gly Phe Ile Glu Asn Gly Trp Glu Gly Met Ile Asp Gly Trp Tyr Gly
            340                 345                 350

Phe Arg His Gln Asn Ser Glu Gly Thr Gly Gln Ala Ala Asp Leu Lys
        355                 360                 365

Ser Thr Gln Ala Ala Ile Asp Gln Ile Asn Gly Lys Leu Asn Arg Val
370                 375                 380

Ile Glu Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Lys Thr Arg Arg Gln Leu Arg Glu Asn Ala Glu Asp Met Gly Asn
450                 455                 460

Gly Cys Phe Lys Ile Tyr His Lys Cys Asp Asn Ala Cys Ile Glu Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val
            500                 505

<210> SEQ ID NO 5
<211> LENGTH: 502
<212> TYPE: PRT
<213> ORGANISM: Influenza A virus (A/Singapore/1/1957(H2N2))

<400> SEQUENCE: 5

Met Asp Gln Ile Cys Ile Gly Tyr His Ala Asn Asn Ser Thr Glu Lys
1               5                   10                  15

Val Asp Thr Ile Leu Glu Arg Asn Val Thr Val Thr His Ala Lys Asp
            20                  25                  30

Ile Leu Glu Lys Thr His Asn Gly Lys Leu Cys Lys Leu Asn Gly Ile
        35                  40                  45

Pro Pro Leu Glu Leu Gly Asp Cys Ser Ile Ala Gly Trp Leu Leu Gly
50                  55                  60

Asn Pro Glu Cys Asp Arg Leu Leu Ser Val Pro Glu Trp Ser Tyr Ile
65                  70                  75                  80

Met Glu Lys Glu Asn Pro Arg Asp Gly Leu Cys Tyr Pro Gly Ser Phe
                85                  90                  95

Asn Asp Tyr Glu Glu Leu Lys His Leu Leu Ser Ser Val Lys His Phe
            100                 105                 110

Glu Lys Val Lys Ile Leu Pro Lys Asp Arg Trp Thr Gln His Thr Thr
        115                 120                 125

Thr Gly Gly Ser Arg Ala Cys Ala Val Ser Gly Asn Pro Ser Phe Phe
130                 135                 140

Arg Asn Met Val Trp Leu Thr Lys Lys Gly Ser Asn Tyr Pro Val Ala
145                 150                 155                 160
```

```
Lys Gly Ser Tyr Asn Asn Thr Ser Gly Glu Gln Met Leu Ile Ile Trp
                165                 170                 175
Gly Val His His Pro Asn Asp Glu Thr Glu Gln Arg Thr Leu Tyr Gln
            180                 185                 190
Asn Val Gly Thr Tyr Val Ser Val Gly Thr Ser Thr Leu Asn Lys Arg
        195                 200                 205
Ser Thr Pro Asp Ile Ala Thr Arg Pro Lys Val Asn Gly Leu Gly Ser
    210                 215                 220
Arg Met Glu Phe Ser Trp Thr Leu Leu Asp Met Trp Asp Thr Ile Asn
225                 230                 235                 240
Phe Glu Ser Thr Gly Asn Leu Ile Ala Pro Glu Tyr Gly Phe Lys Ile
                245                 250                 255
Ser Lys Arg Gly Ser Ser Gly Ile Met Lys Thr Glu Gly Thr Leu Glu
            260                 265                 270
Asn Cys Glu Thr Lys Cys Gln Thr Pro Leu Gly Ala Ile Asn Thr Thr
        275                 280                 285
Leu Pro Phe His Asn Val His Pro Leu Thr Ile Gly Glu Cys Pro Lys
    290                 295                 300
Tyr Val Lys Ser Glu Lys Leu Val Leu Ala Thr Gly Leu Arg Asn Val
305                 310                 315                 320
Pro Gln Ile Glu Ser Arg Gly Leu Phe Gly Ala Ile Ala Gly Phe Ile
                325                 330                 335
Glu Gly Gly Trp Gln Gly Met Val Asp Gly Trp Tyr Gly Tyr His His
            340                 345                 350
Ser Asn Asp Gln Gly Ser Gly Tyr Ala Ala Asp Lys Glu Ser Thr Gln
        355                 360                 365
Lys Ala Phe Asp Gly Ile Thr Asn Lys Val Asn Ser Val Ile Glu Lys
    370                 375                 380
Met Asn Thr Gln Phe Glu Ala Val Gly Lys Glu Phe Ser Asn Leu Glu
385                 390                 395                 400
Arg Arg Leu Glu Asn Leu Asn Lys Lys Met Glu Asp Gly Phe Leu Asp
                405                 410                 415
Val Trp Thr Tyr Asn Ala Glu Leu Leu Val Leu Met Glu Asn Glu Arg
            420                 425                 430
Thr Leu Asp Phe His Asp Ser Asn Val Lys Asn Leu Tyr Asp Lys Val
        435                 440                 445
Arg Met Gln Leu Arg Asp Asn Val Lys Glu Leu Gly Asn Gly Cys Phe
    450                 455                 460
Glu Phe Tyr His Lys Cys Asp Asp Glu Cys Met Asn Ser Val Lys Asn
465                 470                 475                 480
Gly Thr Tyr Asp Tyr Pro Lys Tyr Glu Glu Glu Ser Lys Leu Asn Arg
                485                 490                 495
Asn Glu Ile Lys Gly Val
                500

<210> SEQ ID NO 6
<211> LENGTH: 503
<212> TYPE: PRT
<213> ORGANISM: Influenza A virus (A/Puerto Rico/8/1934(H1N1))

<400> SEQUENCE: 6

Met Asp Thr Ile Cys Ile Gly Tyr His Ala Asn Asn Ser Thr Asp Thr
1               5                   10                  15
Val Asp Thr Val Leu Glu Lys Asn Val Thr Val Thr His Ser Val Asn
            20

-continued

```
Leu Leu Glu Asp Ser His Asn Gly Lys Leu Cys Arg Leu Lys Gly Ile
         35                  40                  45

Ala Pro Leu Gln Leu Gly Lys Cys Asn Ile Ala Gly Trp Leu Leu Gly
 50                  55                  60

Asn Pro Glu Cys Asp Pro Leu Leu Pro Val Arg Ser Trp Ser Tyr Ile
 65                  70                  75                  80

Val Glu Thr Pro Asn Ser Glu Asn Gly Ile Cys Tyr Pro Gly Asp Phe
                     85                  90                  95

Ile Asp Tyr Glu Glu Leu Arg Glu Gln Leu Ser Ser Val Ser Ser Phe
                100                 105                 110

Glu Arg Phe Glu Ile Phe Pro Lys Glu Ser Ser Trp Pro Asn His Asn
            115                 120                 125

Thr Asn Gly Val Thr Ala Ala Cys Ser His Glu Gly Lys Ser Ser Phe
130                 135                 140

Tyr Arg Asn Leu Leu Trp Leu Thr Glu Lys Glu Gly Ser Tyr Pro Asn
145                 150                 155                 160

Leu Lys Asn Ser Tyr Val Asn Lys Lys Gly Lys Glu Val Leu Val Leu
                165                 170                 175

Trp Gly Ile His His Pro Ser Asn Ser Lys Glu Gln Gln Asn Leu Tyr
            180                 185                 190

Gln Asn Glu Asn Ala Tyr Val Ser Val Val Thr Ser Asn Tyr Asn Arg
        195                 200                 205

Arg Phe Thr Pro Glu Ile Ala Glu Arg Pro Lys Val Arg Asp Gln Ala
    210                 215                 220

Gly Arg Met Asn Tyr Tyr Trp Thr Leu Leu Lys Pro Gly Asp Thr Ile
225                 230                 235                 240

Ile Phe Glu Ala Asn Gly Asn Leu Ile Ala Pro Met Tyr Ala Phe Ala
                245                 250                 255

Leu Ser Arg Gly Phe Gly Ser Gly Ile Ile Thr Ser Asn Ala Ser Met
            260                 265                 270

His Glu Cys Asn Thr Lys Cys Gln Thr Pro Leu Gly Ala Ile Asn Ser
        275                 280                 285

Ser Leu Pro Tyr Gln Asn Ile His Pro Val Thr Ile Gly Glu Cys Pro
    290                 295                 300

Lys Tyr Val Arg Ser Ala Lys Leu Arg Met Val Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Ile Asp Gly Trp Tyr Gly Tyr His
            340                 345                 350

His Gln Asn Glu Gln Gly Ser Gly Tyr Ala Ala Asp Gln Lys Ser Thr
        355                 360                 365

Gln Asn Ala Ile Asn Gly Ile Thr Asn Lys Val Asn Thr Val Ile Glu
    370                 375                 380

Lys Met Asn Ile Gln Phe Thr Ala Val Gly Lys Glu Phe Asn Lys Leu
385                 390                 395                 400

Glu Lys Arg Met Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Phe His Asp Ser Asn Val Lys Asn Leu Tyr Glu Lys
        435                 440                 445
```

```
Val Lys Ser Gln Leu Lys Asn Asn Ala Lys Glu Ile Gly Asn Gly Cys
    450                 455                 460
Phe Glu Phe Tyr His Lys Cys Asp Asn Glu Cys Met Glu Ser Val Arg
465                 470                 475                 480
Asn Gly Thr Tyr Asp Tyr Pro Lys Tyr Ser Glu Glu Ser Lys Leu Asn
                485                 490                 495
Arg Glu Lys Val Asp Gly Val
            500

<210> SEQ ID NO 7
<211> LENGTH: 504
<212> TYPE: PRT
<213> ORGANISM: Influenza A virus (A/South Carolina/1/1918(H1N1))

<400> SEQUENCE: 7

Met Asp Thr Ile Cys Ile Gly Tyr His Ala Asn

```
Asn Ile Pro Ser Ile Gln Ser Arg Gly Leu Phe Gly Ala Ile Ala Gly
                325                 330                 335

Phe Ile Glu Gly Gly Trp Thr Gly Met Ile Asp Gly Trp Tyr Gly Tyr
            340                 345                 350

His His Gln Asn Glu Gln Gly Ser Gly Tyr Ala Ala Asp Gln Lys Ser
        355                 360                 365

Thr Gln Asn Ala Ile Asp Gly Ile Thr Asn Lys Val Asn Ser Val Ile
    370                 375                 380

Glu Lys Met Asn Thr Gln Phe Thr Ala Val Gly Lys Glu Phe Asn Asn
385                 390                 395                 400

Leu Glu Arg Arg Ile Glu Asn Leu Asn Lys Lys Val Asp Asp Gly Phe
                405                 410                 415

Leu Asp Ile Trp Thr Tyr Asn Ala Glu Leu Leu Val Leu Leu Glu Asn
            420                 425                 430

Glu Arg Thr Leu Asp Phe His Asp Ser Asn Val Arg Asn Leu Tyr Glu
        435                 440                 445

Lys Val Lys Ser Gln Leu Lys Asn Asn Ala Lys Glu Ile Gly Asn Gly
    450                 455                 460

Cys Phe Glu Phe Tyr His Lys Cys Asp Asp Ala Cys Met Glu Ser Val
465                 470                 475                 480

Arg Asn Gly Thr Tyr Asp Tyr Pro Lys Tyr Ser Glu Glu Ser Lys Leu
                485                 490                 495

Asn Arg Glu Glu Ile Asp Gly Val
            500

<210> SEQ ID NO 8
<211> LENGTH: 320
<212> TYPE: PRT
<213> ORGANISM: Artificial sequence
<220> FEATURE:
<223> OTHER INFORMATION: Synthetic amino acid sequence

<400> SEQUENCE: 8

Met Asp Thr Leu Cys Ile Gly Tyr His Ala Asn Asn Ser Thr Asp Thr
1               5                   10                  15

Val Asp Thr Val Leu Glu Lys Asn Val Thr Val Thr His Ser Val Asn
            20                  25                  30

Leu Leu Glu Asp Lys His Asn Gly Lys Leu Cys Gly Ser Gly Ser Gly
        35                  40                  45

Cys Asn Thr Thr Cys Gln Thr Pro Lys Gly Ala Ile Asn Thr Ser Leu
    50                  55                  60

Pro Phe Gln Asn Ile His Pro Ile Thr Ile Gly Lys Cys Pro Lys Tyr
65                  70                  75                  80

Val Lys Ser Thr Lys Leu Arg Leu Ala Thr Gly Leu Arg Asn Val Pro
                85                  90                  95

Ser Ile Gln Ser Arg Gly Leu Phe Gly Ala Ile Ala Gly Phe Ile Glu
            100                 105                 110

Gly Gly Trp Thr Gly Met Val Asp Gly Trp Tyr Gly Tyr His His Gln
        115                 120                 125

Asn Glu Gln Gly Ser Gly Tyr Ala Ala Asp Leu Lys Ser Thr Gln Asn
    130                 135                 140

Ala Ile Asp Glu Ile Thr Asn Lys Val Asn Ser Val Ile Glu Lys Met
145                 150                 155                 160

Asn Thr Gln Phe Thr Ala Val Gly Lys Glu Phe Asn His Leu Glu Lys
                165                 170                 175
```

Arg Ile Glu Asn Leu Asn Lys Lys Val Asp Asp Gly Phe Leu Asp Ile
            180                 185                 190

Trp Thr Tyr Asn Ala Glu Leu Leu Val Leu Leu Glu Asn Glu Arg Thr
        195                 200                 205

Leu Asp Tyr His Asp Ser Asn Val Lys Asn Leu Tyr Glu Lys Val Arg
    210                 215                 220

Ser Gln Leu Lys Asn Asn Ala Lys Glu Ile Gly Asn Gly Cys Phe Glu
225                 230                 235                 240

Phe Tyr His Lys Cys Asp Asn Thr Cys Met Glu Ser Val Lys Asn Gly
                245                 250                 255

Thr Tyr Asp Tyr Pro Lys Tyr Ser Glu Glu Ala Lys Leu Asn Arg Glu
            260                 265                 270

Glu Ile Asp Gly Val Glu Asn Leu Tyr Phe Gln Ser Gly Ser Gly Tyr
        275                 280                 285

Ile Pro Glu Ala Pro Arg Asp Gly Gln Ala Tyr Val Arg Lys Asp Gly
    290                 295                 300

Glu Trp Val Leu Leu Ser Thr Phe Leu Gly His His His His His His
305                 310                 315                 320

<210> SEQ ID NO 9
<211> LENGTH: 963
<212> TYPE: DNA
<213> ORGANISM: Artificial sequence
<220> FEATURE:
<223> OTHER INFORMATION: Synthetic nucleic acid sequence

<400> SEQUENCE: 9 atggatacc  tctgcattgg  ttaccacgcg  aacaactcca  ccgataccgt  tgacactgtt      60
ctcgaaaaga  acgtgaccgt  gactcactct  gtgaacctgc  tggaagacaa  acataacggt     120
aagctttgcg  gttctggctc  tggttgcaat  actacctgcc  agaccccgaa  aggcgccatt     180
aacacctctc  tcccattcca  gaacatccat  ccaatcacca  ttggcaagtg  tccaaagtat     240
gttaagtcta  ccaaactccg  cctggctacc  ggtctgcgca  atgttccgtc  tattcagtcc     300
cgtggtctgt  tcggcgctat  tgctggcttc  atcgagggcg  gctggactgg  tatggttgac     360
ggctggtacg  gctaccatca  ccagaacgaa  caaggctctg  gctatgcggc  ggacctgaaa     420
tctactcaaa  atgctatcga  cgaaatcact  aataaggtta  attccgtgat  cgaaaaaatg     480
aatactcagg  acactgcggt  tggtaaagaa  ttcaaccacg  acgagaagcg  tattgagaat     540
ctgaacaaaa  aagtggacga  cggttttctc  gacatctgga  cctataacgc  ggaactgctc     600
gtgctcctgg  agaatgaacg  taccctggat  taccatgatt  ctaatgtgaa  gaatctctat     660
gagaaagttc  gctctcagct  caaaaacaat  gcgaaagaaa  tcggtaatgg  ttgcttcgaa     720
ttctaccaca  aatgtgacaa  tacctgcatg  gaatccgtta  agaacggtac  ctacgactac     780
ccaaaatact  ctgaagaagc  gaaactgaac  cgcgaagaga  tcgatggcgt  ggaaaacctg     840
tacttccagt  ctggttctgg  ttacatcccg  gaagctccgc  gtgacggtca  ggcgtacgtt     900
cgtaaagacg  gtgaatgggt  tctgctgtct  accttcctgg  gtcaccacca  tcatcaccac     960
taa                                                                        963

<210> SEQ ID NO 10
<211> LENGTH: 320
<212> TYPE: PRT
<213> ORGANISM: Artificial sequence
<220> FEATURE:
<223> OTHER INFORMATION: Synthetic amino acid sequence

<400> SEQUENCE: 10

```
Met Asp Thr Leu Cys Ile Gly Tyr His Ala Asn Asn Ser Thr Asp Thr
1               5                   10                  15

Val Asp Thr Val Leu Glu Lys Asn Val Thr Val Thr His Ser Val Asn
            20                  25                  30

Leu Leu Glu Asp Lys His Asn Gly Lys Leu Cys Gly Ser Gly Ser Gly
        35                  40                  45

Cys Asn Thr Thr Cys Gln Thr Pro Lys Gly Ala Ile Asn Thr Ser Leu
    50                  55                  60

Pro Phe Gln Asn Thr His Pro Glu Thr Thr Gly Lys Thr Pro Lys Tyr
65                  70                  75                  80

Val Lys Ser Thr Lys Leu Arg Leu Ala Thr Gly Leu Arg Asn Val Pro
                85                  90                  95

Ser Ile Gln Ser Arg Gly Leu Phe Gly Ala Ile Ala Gly Phe Ile Glu
            100                 105                 110

Gly Gly Trp Thr Gly Met Val Asp Gly Trp Tyr Gly Tyr His His Gln
        115                 120                 125

Asn Glu Gln Gly Ser Gly Tyr Ala Ala Asp Leu Lys Ser Thr Gln Asn
130                 135                 140

Ala Ile Asp Glu Ile Thr Asn Lys Val Asn Ser Val Ile Glu Lys Met
145                 150                 155                 160

Asn Thr Gln Phe Thr Ala Val Gly Lys Glu Phe Asn His Leu Glu Lys
                165                 170                 175

Arg Ile Glu Asn Leu Asn Lys Lys Val Asp Asp Gly Phe Leu Asp Ile
            180                 185                 190

Trp Thr Tyr Asn Ala Glu Leu Leu Val Leu Leu Glu Asn Glu Arg Thr
        195                 200                 205

Leu Asp Tyr His Asp Ser Asn Val Lys Asn Leu Tyr Glu Lys Val Arg
    210                 215                 220

Ser Gln Leu Lys Asn Asn Ala Lys Glu Ile Gly Asn Gly Cys Phe Glu
225                 230                 235                 240

Phe Tyr His Lys Cys Asp Asn Thr Cys Met Glu Ser Val Lys Asn Gly
                245                 250                 255

Thr Tyr Asp Tyr Pro Lys Tyr Ser Glu Glu Ala Lys Leu Asn Arg Glu
            260                 265                 270

Glu Ile Asp Gly Val Glu Asn Leu Tyr Phe Gln Ser Gly Ser Gly Tyr
        275                 280                 285

Ile Pro Glu Ala Pro Arg Asp Gly Gln Ala Tyr Val Arg Lys Asp Gly
    290                 295                 300

Glu Trp Val Leu Leu Ser Thr Phe Leu Gly His His His His His His
305                 310                 315                 320
```

<210> SEQ ID NO 11
<211> LENGTH: 320
<212> TYPE: PRT
<213> ORGANISM: Artificial sequence
<220> FEATURE:
<223> OTHER INFORMATION: Synthetic amino acid sequence

<400> SEQUENCE: 11

```
Met Asp Thr Leu Cys Ile Gly Tyr His Ala Asn Asn Ser Thr Asp Thr
1               5                   10                  15

Val Asp Thr Val Leu Glu Lys Asn Val Thr Val Thr His Ser Val Asn
            20                  25                  30
```

-continued

```
Leu Leu Glu Asp Lys His Asn Gly Lys Leu Cys Gly Ser Gly Ser Gly
         35                  40                  45

Cys Asn Thr Thr Cys Gln Thr Pro Lys Gly Ala Ile Asn Thr Ser Leu
 50                  55                  60

Pro Phe Gln Asn Thr His Pro Glu Thr Thr Gly Lys Thr Pro Lys Tyr
 65                  70                  75                  80

Val Lys Ser Thr Lys Leu Arg Leu Ala Thr Gly Leu Arg Asn Val Pro
                 85                  90                  95

Ser Ile Gln Ser Arg Gly Leu Phe Gly Ala Ile Ala Gly Phe Ile Glu
                100                 105                 110

Gly Gly Trp Thr Gly Met Val Asp Gly Trp Tyr Gly Tyr His His Gln
            115                 120                 125

Asn Glu Gln Gly Ser Gly Tyr Ala Ala Asp Leu Lys Ser Thr Gln Asn
130                 135                 140

Ala Ile Asp Glu Ile Thr Asn Lys Val Asn Ser Val Ile Glu Lys Met
145                 150                 155                 160

Asn Thr Gln Asp Thr Ala Val Gly Lys Glu Phe Asn His Leu Glu Lys
                165                 170                 175

Arg Ile Glu Asn Leu Asn Lys Lys Val Asp Asp Gly Phe Leu Asp Ile
                180                 185                 190

Trp Thr Tyr Asn Ala Glu Leu Leu Val Leu Leu Glu Asn Glu Arg Thr
            195                 200                 205

Leu Asp Tyr His Asp Ser Asn Val Lys Asn Leu Tyr Glu Lys Val Arg
210                 215                 220

Ser Gln Leu Lys Asn Asn Ala Lys Glu Ile Gly Asn Gly Cys Phe Glu
225                 230                 235                 240

Phe Tyr His Lys Cys Asp Asn Thr Cys Met Glu Ser Val Lys Asn Gly
                245                 250                 255

Thr Tyr Asp Tyr Pro Lys Tyr Ser Glu Glu Ala Lys Leu Asn Arg Glu
                260                 265                 270

Glu Ile Asp Gly Val Glu Asn Leu Tyr Phe Gln Ser Gly Ser Gly Tyr
            275                 280                 285

Ile Pro Glu Ala Pro Arg Asp Gly Gln Ala Tyr Val Arg Lys Asp Gly
290                 295                 300

Glu Trp Val Leu Leu Ser Thr Phe Leu Gly His His His His His His
305                 310                 315                 320
```

<210> SEQ ID NO 12
<211> LENGTH: 320
<212> TYPE: PRT
<213> ORGANISM: Artificial sequence
<220> FEATURE:
<223> OTHER INFORMATION: Synthetic amino acid sequence

<400> SEQUENCE: 12

```
Met Asp Thr Leu Cys Ile Gly Tyr His Ala Asn Asn Ser Thr Asp Thr
 1               5                  10                  15

Val Asp Thr Val Leu Glu Lys Asn Val Thr Val Thr His Ser Val Asn
                 20                  25                  30

Leu Leu Glu Asp Lys His Asn Gly Lys Leu Cys Gly Ser Gly Ser Gly
             35                  40                  45

Cys Asn Thr Thr Cys Gln Thr Pro Lys Gly Ala Ile Asn Thr Ser Leu
 50                  55                  60

Pro Phe Gln Asn Thr His Pro Glu Thr Thr Gly Lys Thr Pro Lys Tyr
 65                  70                  75                  80
```

Val Lys Ser Thr Lys Leu Arg Leu Ala Thr Gly Leu Arg Asn Val Pro
            85                  90                  95

Ser Ile Gln Ser Arg Gly Leu Phe Gly Ala Ile Ala Gly Phe Ile Glu
            100                 105                 110

Gly Gly Trp Thr Gly Met Val Asp Gly Trp Tyr Gly Tyr His His Gln
            115                 120                 125

Asn Glu Gln Gly Ser Gly Tyr Ala Ala Asp Leu Lys Ser Thr Gln Asn
            130                 135                 140

Ala Ile Asp Glu Ile Thr Asn Lys Val Asn Ser Val Ile Glu Lys Met
145                 150                 155                 160

Asn Thr Gln Asp Thr Ala Val Gly Lys Glu Phe Asn His Asp Glu Lys
            165                 170                 175

Arg Ile Glu Asn Leu Asn Lys Lys Val Asp Asp Gly Phe Leu Asp Ile
            180                 185                 190

Trp Thr Tyr Asn Ala Glu Leu Leu Val Leu Leu Glu Asn Glu Arg Thr
            195                 200                 205

Leu Asp Tyr His Asp Ser Asn Val Lys Asn Leu Tyr Glu Lys Val Arg
            210                 215                 220

Ser Gln Leu Lys Asn Asn Ala Lys Glu Ile Gly Asn Gly Cys Phe Glu
225                 230                 235                 240

Phe Tyr His Lys Cys Asp Asn Thr Cys Met Glu Ser Val Lys Asn Gly
            245                 250                 255

Thr Tyr Asp Tyr Pro Lys Tyr Ser Glu Glu Ala Lys Leu Asn Arg Glu
            260                 265                 270

Glu Ile Asp Gly Val Glu Asn Leu Tyr Phe Gln Ser Gly Ser Gly Tyr
            275                 280                 285

Ile Pro Glu Ala Pro Arg Asp Gly Gln Ala Tyr Val Arg Lys Asp Gly
290                 295                 300

Glu Trp Val Leu Leu Ser Thr Phe Leu Gly His His His His His His
            305                 310                 315                 320

<210> SEQ ID NO 13
<211> LENGTH: 320
<212> TYPE: PRT
<213> ORGANISM: Artificial sequence
<220> FEATURE:
<223> OTHER INFORMATION: Synthetic amino acid sequence

<400> SEQUENCE: 13

Met Asp Thr Leu Cys Ile Gly Tyr His Ala Asn Asn Ser Thr Asp Thr
1               5                   10                  15

Val Asp Thr Val Leu Glu Lys Asn Val Thr Val Thr His Ser Val Asn
            20                  25                  30

Leu Leu Glu Asp Lys His Asn Gly Lys Leu Cys Gly Ser Gly Ser Gly
            35                  40                  45

Cys Asn Thr Thr Cys Gln Thr Pro Lys Gly Ala Ile Asn Thr Ser Leu
50                  55                  60

Pro Phe Gln Asn Ile His Pro Ile Thr Ile Gly Lys Cys Pro Lys Tyr
65                  70                  75                  80

Val Lys Ser Thr Lys Leu Arg Leu Ala Thr Gly Leu Arg Asn Val Pro
            85                  90                  95

Ser Ile Gln Ser Arg Gly Leu Phe Gly Ala Ile Ala Gly Phe Ile Glu
            100                 105                 110

Gly Gly Trp Thr Gly Met Val Asp Gly Trp Tyr Gly Tyr His His Gln
            115                 120                 125

```
Asn Glu Gln Gly Ser Gly Tyr Ala Ala Asp Leu Lys Ser Thr Gln Asn
    130                 135                 140

Ala Ile Asp Glu Ile Thr Asn Lys Val Asn Ser Val Ile Glu Lys Met
145                 150                 155                 160

Asn Thr Gln Asp Thr Ala Val Gly Lys Glu Phe Asn His Leu Glu Lys
                165                 170                 175

Arg Ile Glu Asn Leu Asn Lys Lys Val Asp Asp Gly Phe Leu Asp Ile
            180                 185                 190

Trp Thr Tyr Asn Ala Glu Leu Leu Val Leu Leu Glu Asn Glu Arg Thr
        195                 200                 205

Leu Asp Tyr His Asp Ser Asn Val Lys Asn Leu Tyr Glu Lys Val Arg
    210                 215                 220

Ser Gln Leu Lys Asn Asn Ala Lys Glu Ile Gly Asn Gly Cys Phe Glu
225                 230                 235                 240

Phe Tyr His Lys Cys Asp Asn Thr Cys Met Glu Ser Val Lys Asn Gly
                245                 250                 255

Thr Tyr Asp Tyr Pro Lys Tyr Ser Glu Glu Ala Lys Leu Asn Arg Glu
            260                 265                 270

Glu Ile Asp Gly Val Glu Asn Leu Tyr Phe Gln Ser Gly Ser Gly Tyr
        275                 280                 285

Ile Pro Glu Ala Pro Arg Asp Gly Gln Ala Tyr Val Arg Lys Asp Gly
    290                 295                 300

Glu Trp Val Leu Leu Ser Thr Phe Leu Gly His His His His His His
305                 310                 315                 320

<210> SEQ ID NO 14
<211> LENGTH: 320
<212> TYPE: PRT
<213> ORGANISM: Artificial sequence
<220> FEATURE:
<223> OTHER INFORMATION: Synthetic amino acid sequence

<400> SEQUENCE: 14

Met Asp Thr Leu Cys Ile Gly Tyr His Ala Asn Asn Ser Thr Asp Thr
1               5                   10                  15

Val Asp Thr Val Leu Glu Lys Asn Val Thr Val Thr His Ser Val Asn
                20                  25                  30

Leu Leu Glu Asp Lys His Asn Gly Lys Leu Cys Gly Ser Gly Ser Gly
            35                  40                  45

Cys Asn Thr Thr Cys Gln Thr Pro Lys Gly Ala Ile Asn Thr Ser Leu
        50                  55                  60

Pro Phe Gln Asn Ile His Pro Ile Thr Ile Gly Lys Cys Pro Lys Tyr
65                  70                  75                  80

Val Lys Ser Thr Lys Leu Arg Leu Ala Thr Gly Leu Arg Asn Val Pro
                85                  90                  95

Ser Ile Gln Ser Arg Gly Leu Phe Gly Ala Ile Ala Gly Phe Ile Glu
            100                 105                 110

Gly Gly Trp Thr Gly Met Val Asp Gly Trp Tyr Gly Tyr His His Gln
        115                 120                 125

Asn Glu Gln Gly Ser Gly Tyr Ala Ala Asp Leu Lys Ser Thr Gln Asn
    130                 135                 140

Ala Ile Asp Glu Ile Thr Asn Lys Val Asn Ser Val Ile Glu Lys Met
145                 150                 155                 160

Asn Thr Gln Asp Thr Ala Val Gly Lys Glu Phe Asn His Asp Glu Lys
                165                 170                 175
```

```
Arg Ile Glu Asn Leu Asn Lys Lys Val Asp Asp Gly Phe Leu Asp Ile
            180                 185                 190

Trp Thr Tyr Asn Ala Glu Leu Leu Val Leu Leu Glu Asn Glu Arg Thr
        195                 200                 205

Leu Asp Tyr His Asp Ser Asn Val Lys Asn Leu Tyr Glu Lys Val Arg
    210                 215                 220

Ser Gln Leu Lys Asn Asn Ala Lys Glu Ile Gly Asn Gly Cys Phe Glu
225                 230                 235                 240

Phe Tyr His Lys Cys Asp Asn Thr Cys Met Glu Ser Val Lys Asn Gly
                245                 250                 255

Thr Tyr Asp Tyr Pro Lys Tyr Ser Glu Glu Ala Lys Leu Asn Arg Glu
            260                 265                 270

Glu Ile Asp Gly Val Glu Asn Leu Tyr Phe Gln Ser Gly Ser Gly Tyr
        275                 280                 285

Ile Pro Glu Ala Pro Arg Asp Gly Gln Ala Tyr Val Arg Lys Asp Gly
    290                 295                 300

Glu Trp Val Leu Leu Ser Thr Phe Leu Gly His His His His His His
305                 310                 315                 320

<210> SEQ ID NO 15
<211> LENGTH: 320
<212> TYPE: PRT
<213> ORGANISM: Artificial sequence
<220> FEATURE:
<223> OTHER INFORMATION: Synthetic amino acid sequence

<400> SEQUENCE: 15

Met Asp Thr Leu Cys Ile Gly Tyr His Ala Asn Asn Ser Thr Asp Thr
1               5                   10                  15

Val Asp Thr Val Leu Glu Lys Asn Val Thr Val Thr His Ser Val Asn
            20                  25                  30

Leu Leu Glu Asp Lys His Asn Gly Lys Leu Cys Gly Ser Gly Ser Gly
        35                  40                  45

Cys Asn Thr Thr Cys Gln Thr Pro Lys Gly Ala Ile Asn Thr Ser Leu
50                  55                  60

Pro Phe Gln Asn Ile His Pro Ile Thr Ile Gly Lys Cys Pro Lys Tyr
65                  70                  75                  80

Val Lys Ser Thr Lys Leu Arg Leu Ala Thr Gly Leu Arg Asn Val Pro
                85                  90                  95

Ser Ile Gln Ser Arg Gly Leu Phe Gly Ala Ile Ala Gly Phe Ile Glu
            100                 105                 110

Gly Gly Trp Thr Gly Met Val Asp Gly Trp Tyr Gly Tyr His His Gln
        115                 120                 125

Asn Glu Gln Gly Ser Gly Tyr Ala Ala Asp Leu Lys Ser Thr Gln Asn
    130                 135                 140

Ala Ile Asp Glu Ile Thr Asn Lys Val Asn Ser Val Ile Glu Lys Met
145                 150                 155                 160

Asn Thr Gln Asp Thr Ala Val Gly Lys Glu Phe Asn His Asp Glu Lys
                165                 170                 175

Arg Ile Glu Asn Leu Asn Lys Lys Val Asp Asp Gly Phe Leu Asp Ile
            180                 185                 190

Trp Thr Tyr Asn Ala Glu Leu Leu Val Leu Leu Glu Asn Glu Arg Thr
        195                 200                 205

Leu Asp Tyr His Asp Ser Asn Val Lys Asn Leu Tyr Glu Lys Val Arg
    210                 215                 220
```

```
Ser Gln Leu Lys Asn Asn Ala Lys Glu Ile Gly Asn Gly Cys Phe Glu
225                 230                 235                 240

Phe Tyr His Lys Cys Asp Asn Thr Cys Met Glu Ser Val Lys Asn Gly
                245                 250                 255

Thr Tyr Asp Tyr Pro Lys Tyr Ser Glu Glu Ala Lys Leu Asn Arg Glu
            260                 265                 270

Glu Ile Asp Gly Val Glu Asn Leu Tyr Phe Gln Ser Gly Ser Gly Tyr
        275                 280                 285

Ile Pro Glu Ala Pro Arg Asp Gly Gln Ala Tyr Val Arg Lys Asp Gly
290                 295                 300

Glu Trp Val Leu Leu Ser Thr Phe Leu Gly His His His His His His
305                 310                 315                 320

<210> SEQ ID NO 16
<211> LENGTH: 301
<212> TYPE: PRT
<213> ORGANISM: Artificial sequence
<220> FEATURE:
<223> OTHER INFORMATION: Synthetic amino acid sequence

<400> SEQUENCE: 16

Met Asp Thr Leu Cys Ile Gly Tyr His Ala Asn Asn Ser Thr Asp Thr
1               5                   10                  15

Val Asp Thr Val Leu Glu Lys Asn Val Thr Val Thr His Ser Val Asn
            20                  25                  30

Leu Leu Glu Asp Lys Gly Ser Gly Ser Gly Thr Ser Leu Pro Phe Gln
        35                  40                  45

Asn Ile His Pro Ile Thr Ile Gly Lys Thr Pro Lys Tyr Val Lys Ser
    50                  55                  60

Thr Lys Leu Arg Leu Ala Thr Gly Leu Arg Asn Val Pro Ser Ile Gln
65                  70                  75                  80

Ser Arg Gly Leu Phe Gly Ala Ile Ala Gly Phe Ile Glu Gly Gly Trp
                85                  90                  95

Thr Gly Met Val Asp Gly Trp Tyr Gly Tyr His His Gln Asn Glu Gln
            100                 105                 110

Gly Ser Gly Tyr Ala Ala Asp Leu Lys Ser Thr Gln Asn Ala Ile Asp
        115                 120                 125

Glu Ile Thr Asn Lys Val Asn Ser Val Ile Glu Lys Met Asn Thr Gln
    130                 135                 140

Asp Thr Ala Val Gly Lys Glu Phe Asn His Asp Glu Lys Arg Ile Glu
145                 150                 155                 160

Asn Leu Asn Lys Lys Val Asp Asp Gly Phe Leu Asp Ile Trp Thr Tyr
                165                 170                 175

Asn Ala Glu Leu Leu Val Leu Leu Glu Asn Glu Arg Thr Leu Asp Tyr
            180                 185                 190

His Asp Ser Asn Val Lys Asn Leu Tyr Glu Lys Val Arg Ser Gln Leu
        195                 200                 205

Lys Asn Asn Ala Lys Glu Ile Gly Asn Gly Cys Phe Glu Phe Tyr His
    210                 215                 220

Lys Cys Asp Asn Thr Cys Met Glu Ser Val Lys Asn Gly Thr Tyr Asp
225                 230                 235                 240

Tyr Pro Lys Tyr Ser Glu Glu Ala Lys Leu Asn Arg Glu Glu Ile Asp
                245                 250                 255

Gly Val Glu Asn Leu Tyr Phe Gln Ser Gly Ser Gly Tyr Ile Pro Glu
            260                 265                 270
```

Ala Pro Arg Asp Gly Gln Ala Tyr Val Arg Lys Asp Gly Glu Trp Val
            275                 280                 285

Leu Leu Ser Thr Phe Leu Gly His His His His His His
        290                 295                 300

<210> SEQ ID NO 17
<211> LENGTH: 26
<212> TYPE: PRT
<213> ORGANISM: Artificial sequence
<220> FEATURE:
<223> OTHER INFORMATION: Synthetic amino acid sequence

<400> SEQUENCE: 17

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe
            20                  25

<210> SEQ ID NO 18
<211> LENGTH: 250
<212> TYPE: PRT
<213> ORGANISM: Artificial sequence
<220> FEATURE:
<223> OTHER INFORMATION: Synthetic amino acid sequence

<400> SEQUENCE: 18

Met Asp Leu Pro Gly Asn Asp Asn Ser Met Asp Thr Ile Cys Ile Gly
1               5                   10                  15

Tyr His Ala Asn Asn Ser Thr Val Asp Thr Leu Glu Lys Asn Val Thr
            20                  25                  30

Val Thr His Leu Leu Glu His Asn Gly Lys Leu Cys Cys Asn Thr Lys
        35                  40                  45

Cys Gln Thr Pro Gly Ala Ile Asn Ser Leu Pro Phe Gln Asn Ile His
    50                  55                  60

Pro Thr Ile Gly Glu Cys Pro Lys Tyr Val Lys Ser Lys Leu Leu Ala
65                  70                  75                  80

Thr Gly Leu Arg Asn Pro Ile Gln Ser Arg Gly Leu Phe Gly Ala Ile
                85                  90                  95

Ala Gly Phe Ile Glu Gly Gly Trp Gly Met Asp Gly Trp Tyr Gly Tyr
            100                 105                 110

His His Gln Asn Glu Gln Gly Ser Gly Tyr Ala Ala Asp Lys Ser Thr
        115                 120                 125

Gln Ala Ile Asp Gly Ile Thr Asn Lys Val Asn Ser Val Ile Glu Lys
    130                 135                 140

Met Asn Thr Gln Phe Ala Val Gly Lys Glu Phe Asn Leu Glu Arg Ile
145                 150                 155                 160

Glu Asn Leu Asn Lys Lys Val Asp Gly Phe Leu Asp Trp Thr Tyr Asn
                165                 170                 175

Ala Glu Leu Leu Val Leu Leu Glu Asn Glu Arg Thr Leu Asp Phe His
            180                 185                 190

Asp Ser Asn Val Lys Asn Leu Tyr Glu Lys Val Arg Gln Leu Asn Ala
        195                 200                 205

Lys Glu Gly Asn Gly Cys Phe Glu Phe Tyr His Lys Cys Asp Asn Cys
    210                 215                 220

```
Met Glu Ser Val Arg Asn Gly Thr Tyr Asp Tyr Pro Lys Tyr Ser Glu
225                 230                 235                 240

Glu Lys Leu Asn Arg Glu Glu Ile Gly Val
                245                 250
```

INFLUENZA VACCINE CONSTRUCTS

FEDERALLY SPONSORED RESEARCH AND DEVELOPMENT

This invention was made with Government support under contract AI057229 awarded by the National Institutes of Health. The Government has certain rights in the invention.

BACKGROUND OF THE INVENTION

Influenza is a major global public health challenge. Although several different influenza vaccines and drugs are available to prevent and treat influenza, in the United States alone each year there are 25-50 million cases of influenza and 30,000 to 40,000 deaths. Controlling seasonal influenza A virus is a challenge because of rapid viral spread; short incubation period; and changing antigenicity of the viral glycoproteins.

Influenza A viruses are negative sense, single-stranded, segmented RNA viruses of the Orthomyxoviridae family. There are several subtypes, labeled according to an H number (for the type of hemagglutinin) and an N number (for the type of neuraminidase). There are 16 different H antigens (H1 to H16) and nine different N antigens (N1 to N9). Each virus subtype has mutated into a variety of strains with differing pathogenic profiles; some are pathogenic to one species but not others, some are pathogenic to multiple species.

The segmentation of the influenza A genome facilitates reassortment among strains, when two or more strains infect the same cell. Reassortment can yield major genetic changes, referred to as antigenic shifts. In contrast, antigenic drift is the accumulation of viral strains with minor genetic changes, mainly amino acid substitutions in the HA and NA proteins. Influenza A nucleic acid replication by the virus-encoded RNA-dependent RNA polymerase complex is relatively error-prone, and these point mutations in the RNA genome are the major source of genetic variation for antigenic drift. Selection favors human influenza A strains with antigenic drift and shift involving the HA and NA proteins because these strains are then able to evade neutralizing antibody from prior infection or vaccination. Antigenic shifts caused three of the major influenza A pandemics in the twentieth century, while antigenic drift accounts for the annual nature of flu epidemics.

Hemagglutinin A is involved in viral attachment to terminal sialic acid residues on host cell glycoproteins and glycolipids. After viral entry into an acidic endosomal compartment of the cell, HA is also involved in fusion with the cell membrane. HA is synthesized as an $HA_0$ precursor that forms noncovalently bound homotrimers on the viral surface, which is cleaved by host proteases to create two subunits associated by a single disulfide bond. The mature HA forms homotrimers having a long fibrous stem comprised of a triple-stranded coiled coil of α-helices derived from the HA2 domains, and a globular head derived from the HA1 domains.

Vaccines that provide for effective protection against influenza infection, and that can address a rapidly evolving virus, are of great medical interest. The present invention addresses this issue.

RELEVANT LITERATURE

Publications relating to the use of foldon in the construction of influenza vaccines include, inter alia, US 2009/0208531. Publications relating to the use of the HA stem in the construction of influenza vaccines may be found, for example in US 2012/0014972 and in US 2010/0297174, each herein specifically incorporated by reference.

Methods of introducing unnatural amino acids during CFPS are described in patent publication US 2010-0093024 A1. Methods of directly linking antigens and other polypeptides to a virus-like particle through unnatural amino acids are described in patent application US-2010-0168402-A1. Methods of encapsidating cargo into virus-like particles produced by CFPS are described in patent publication US-2010-0167981-A1. Each of these documents are herein specifically incorporated by reference.

SUMMARY OF THE INVENTION

Vaccine compositions are provided comprising a trimeric influenza hemagglutinin (HA) stem antigen. The sequence of the HA antigen is modified from the wild-type by the substitution of one or more hydrophobic amino acid residues with polar amino acids, particularly the substitution of hydrophobic residues in the exposed domain, with polar amino acids. The sequence is further modified by the deletion of polypeptide regions in the stem containing hydrophobic residues and cysteines. The modified HA antigen is fused to a trimerization domain, including without limitation, T4 bacteriophage fibritin foldon. In some embodiments the sequence is modified to allow the introduction of unnatural amino acids useful in linking the antigen to a virus-like particle (VLP), where a defined unnatural amino acid may be positioned at the terminus of the trimerization domain, or outside of the helical structure of the HA stem. In additional embodiments the sequence is modified to include a motif useful in protein purification, e.g. a histidine tag, a protease cleavage site and the like.

The fusion proteins of this invention can be made by transforming host cells with nucleic acid encoding the fusion, culturing the host cell and recovering the fusion from the culture, or alternatively by generating a nucleic acid construct encoding the fusion and producing the polypeptide by cell free synthesis, which synthesis may include coupled transcription and translation reactions. Also provided are vectors and polynucleotides encoding the fusion protein.

In one embodiment of the invention, a method is provided for the cell-free protein synthesis (CFPS) of the fusion protein of the invention. In some embodiments the CFPS product is isolated from the reaction mixture and refolded prior to formulation. In some embodiments the refolding is performed in the presence of a detergent, usually a nonionic detergent. The detergent may be present at a concentration of from about 0.01 to 0.1%, usually around 0.05%. Detergents of interest include nonionic polyoxyethylene surfactants, e.g. Brij 35; Tween 20, etc.

The fusion proteins may be purified and formulated in pharmacologically acceptable vehicles for administration to a patient. In some embodiments the fusion proteins are linked to a VLP for formulation. In some embodiments the VLP comprises proteins in addition to the HA antigen, which proteins may include, without limitation, adjuvants, e.g. GM-CSF, etc., additional influenza antigens, etc.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 19. Procedure IV (for mutant M6).

FIG. 20. Table 3. The isoelectric point analysis of HA stem fragments with different mutations.

DETAILED DESCRIPTION OF THE EMBODIMENTS

Figure 1:
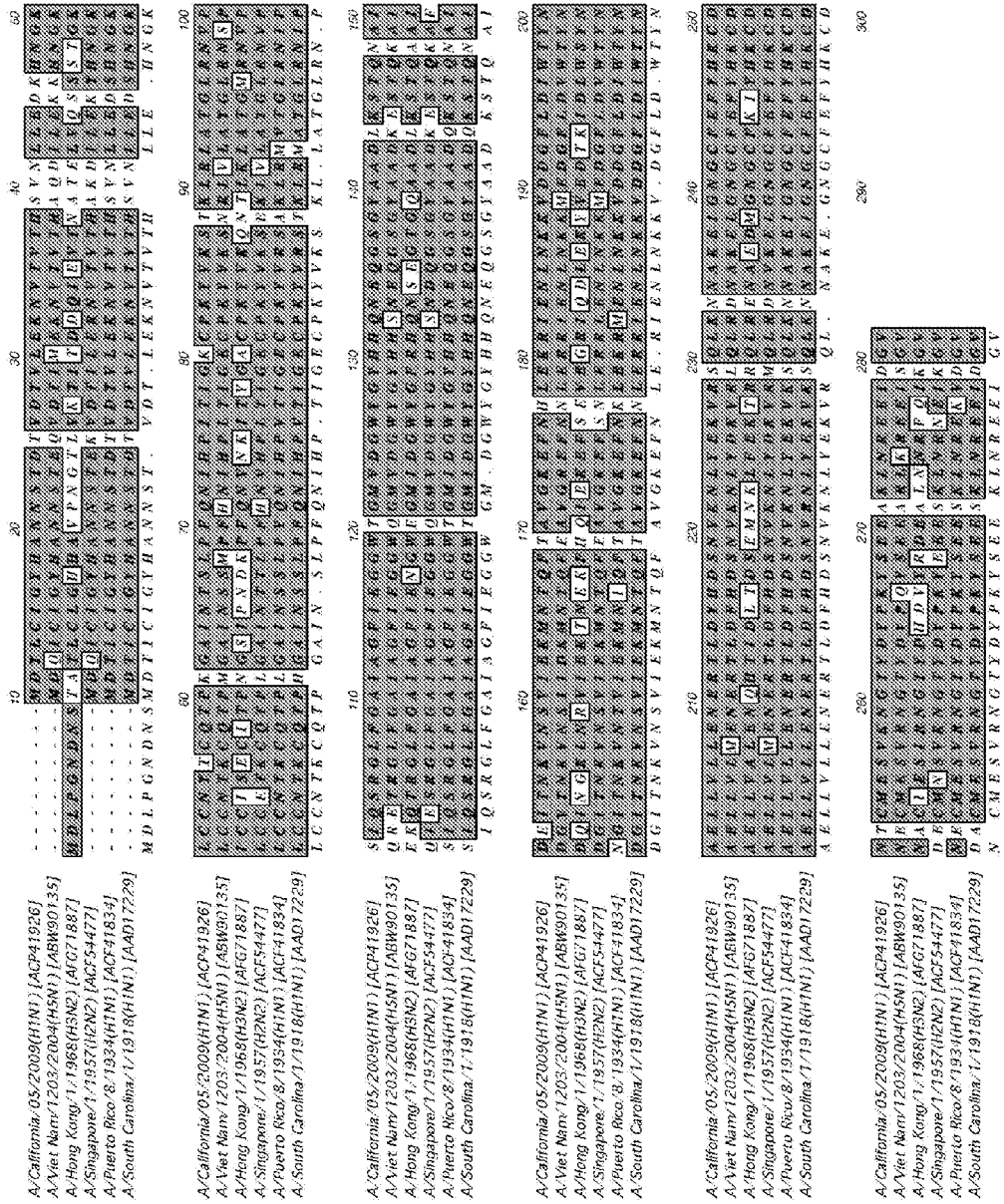
FIG. 1 Sequence alignment of HA stem domain from 6 different HA variants. The residues with H3 stem domain numbering are: A/California/05/2009 (H1N1), 18-59, 292-520; A/Viet Nam/1203/2004(H5N1), 17-58, 290-518; A/Hong Kong/1/1968(H3N2), 18-68, 293-521; A/Singapore/1/1957(H2N2), 16-57, 288-516; A/Puerto Rico/8/1934 (H1N1), 18-59, 291-519; and A/South Carolina/1/1918 (H1N1), 18-59, 292-520.

The present invention is directed to immunogenic influenza virus HA compositions and methods useful for the induction and/or enhancement of an immune response against influenza. In some embodiments, the invention provides a method of inducing an immune response against influenza virus HA protein, comprising contacting a mammal with a composition, conjugate or compound described herein. In other embodiments, the invention provides a method of preventing an influenza virus infection or attenuating the virulence of an influenza virus infection, comprising administering to a subject an effective amount of a composition, conjugate or compound described herein.

In some embodiments, the invention provides a use of a conjugate, compound, or composition herein in the manufacture of a medicament. In an embodiment, the invention provides a use of a conjugate, compound, or composition herein in the manufacture of a medicament for the prevention or treatment of an influenza virus infection. In some embodiments, the invention provides a use of a conjugate, compound, or composition herein for the prevention or treatment of an influenza virus infection.

An antigenic polypeptide of the invention comprises the stem domain of an influenza HA protein, e.g. an influenza A HA protein or fraction thereof, modified to reduce hydrophobicity in exposed residues and to decrease the number of cysteines. The HA protein is fused to a trimerization domain. The HA1 and HA2 domains will be arranged in the order shown while other domains may be arranged in the fusion protein in any order, and may further comprise one or more flexible linker sequences, protease cleavage sites, tags for purification, and the like. Proteins for use in the invention may be purified and formulated in pharmacologically acceptable vehicles for administration to a patient.

The fusion proteins of this invention can be made by transforming host cells with nucleic acid encoding the fusion, culturing the host cell and recovering the fusion from the culture, or alternatively by generating a nucleic acid construct encoding the fusion and producing the polypeptide by cell free synthesis, which synthesis may include coupled transcription and translation reactions.

DEFINITIONS

"Hemagglutinin" and "HA" refer to any hemagglutinin known to those of skill in the art. In certain embodiments, the hemagglutinin is influenza hemagglutinin, such as an influenza A hemagglutinin, an influenza B hemagglutinin or an influenza C hemagglutinin. A native hemagglutinin protein typically comprises a signal peptide, a stem domain, a globular head domain, a luminal domain, a transmembrane domain and a cytoplasmic domain. For the purposes of the present invention, modified HA stem domains are utilized. As used herein, the terms "hemagglutinin" and "HA" encompass hemagglutinin polypeptides that are modified by post-translational processing such as signal peptide cleavage, disulfide bond formation, glycosylation (e.g., N-linked glycosylation), protease cleavage and lipid modification (e.g. S-palmitoylation).

"HA1 N-terminal stem segment" refers to a polypeptide segment that corresponds to the amino-terminal portion of the stem domain of an influenza hemagglutinin HA1 polypeptide. In certain embodiments, an HA1 N-terminal stem segment consists of amino acid residues corresponding approximately to amino acids 18 to 58 or 18 to 68 of an HA1 domain.

The HA1 C-terminal stem segment might be any HA1 stem segment recognized by one of skill in the art based on the definition provided herein. Typically, an HA1 stem segment corresponds to a polypeptide consisting of the cysteine residue located in sequence at approximately the $277^{th}$ residue of an HA amino acid sequence through the C-terminal amino acid of the HA1. This segment may correspond approximately to, for example, residues 292 to 520.

Trimerization domains are known in the art and have been successfully used to promote stable trimers of soluble recombinant proteins. Domains include GCN4 leucine zipper (Harbury et al. 1993 *Science* 262:1401-1407), trimerization domain from the lung surfactant protein (Hoppe et al. 1994 *FEBS Lett* 344:191-195), collagen (McAlinden et al. 2003 *J Biol Chem* 278:42200-42207), and the phage T4 fibritin 'foldon' (Miroshnikov et al. 1998 *Protein Eng* 11:329-414).

The term "foldon" or "foldon domain" refers to the C-terminal amino acid peptide sequence of the bacteriophage T4 fibritin sequence or portions thereof, or fragments thereof having foldon activity. Foldon is capable of forming a trimeric structure. Foldon activity refers to the ability of foldon to form trimers. In one aspect, foldon refers to the amino acid sequence of SEQ ID NO: GYIPEAPRDGQAYVRKDGEWVLLSTF or any fragments or variants thereof having foldon activity. Foldon adopts a β-propeller conformation, and can fold and trimerize in an autonomous way.

As used herein, the terms "purified" and "isolated" when used in the context of a polypeptide that is substantially free of contaminating materials from the material from which it was obtained, e.g. cellular materials, such as but not limited to cell debris, cell wall materials, membranes, organelles, the bulk of the nucleic acids, carbohydrates, proteins, and/or lipids present in cells. Thus, a polypeptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a polypeptide that is chemically synthesized refers to a polypeptide which is substantially free of chemical precursors or other chemicals which are involved in the syntheses of the polypeptide. In some embodiments, an influenza hemagglutinin stem domain polypeptide of the invention is produced by cell-free protein synthesis. In other specific embodiments, an influenza hemagglutinin stem domain polypeptide of the invention is produced by recombinant methods in a cell.

As used herein, the terms "subject" or "patient" are used interchangeably to refer to an animal (e.g., birds, reptiles, and mammals). In some embodiments, a subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, a subject is a non-human animal. In some embodiments, a subject is a farm animal or pet. In another embodiment, a subject is a human, e.g. a human infant including premature infants, child, adult, and/or elderly human.

An "immunogenic composition" or an "antigenic composition" as used herein refers to a combination of modified influenza HA stem domain fused to a trimerization domain, and optionally in combination with one or more flexible linkers, protease cleavage sites, and or purification tags. Such a composition elicits an HA specific immune response when administered to a host.

As used herein, the term "epitope" refers to a molecule (or association of molecules), containing a region capable of eliciting an immune response and/or containing a region capable of specific binding with an antibody. An epitope may be selected, for example, from a portion of a protein not previously known to bind specifically to an antibody.

The term "polypeptide," "peptide," "oligopeptide," and "protein," are used interchangeably herein, and refer to a polymeric form of amino acids of any length, which can include coded and non-coded amino acids, chemically, or biochemically modified or derivatized amino acids, and polypeptides having modified peptide backbones.

By "fused" or "operably linked" herein is meant that two or more polypeptides are linked together to form a continuous polypeptide chain. As outlined in the Examples, the fusion polypeptide (or fusion polynucleotide encoding the fusion polypeptide) can comprise further components as well, including multiple peptides at multiple loops, fusion partners, etc. The precise site at which the fusion is made is not critical; particular sites are well known and may be selected in order to optimize the biological activity, secretion or binding characteristics of the binding partner. The optimal site will be determined by routine experimentation.

The term "immune response" refers to any response to an antigenic or immunogenic compound by the immune system of a vertebrate subject. Exemplary immune responses include, but are not limited to local and systemic cellular as well as humoral immunity, such as cytotoxic T lymphocyte (CTL) responses, including antigen-specific induction of $CD8^+$ CTLs, helper T-cell responses including T-cell proliferative responses and cytokine release, and B-cell responses including antibody response.

The term "eliciting an immune response" is used herein generally to encompass induction and/or potentiation of an immune response.

The term "inducing an immune response" refers to an immune response that is stimulated, initiated, or induced.

The term "potentiating an immune response" refers to a pre-existing immune response that is improved, furthered, supplemented, amplified, enhanced, increased or prolonged.

The expression "enhanced immune response" or similar means that the immune response is elevated, improved or enhanced to the benefit of the host relative to the prior immune response status, for example, before the administration of an immunogenic composition of the invention.

The terms "humoral immunity" and "humoral immune response" refer to the form of immunity in which antibody molecules are produced in response to antigenic stimulation.

The terms "cell-mediated immunity" and "cell-mediated immune response" are meant to refer to the immunological defense provided by lymphocytes, such as that defense provided by T cell lymphocytes when they come into close proximity to their victim cells. A cell-mediated immune response normally includes lymphocyte proliferation. When "lymphocyte proliferation" is measured, the ability of lymphocytes to proliferate in response to a specific antigen is measured. Lymphocyte proliferation is meant to refer to B cell, T-helper cell or cytotoxic T-lymphocyte (CTL) cell proliferation.

The term "immunogenic amount" refers to an amount of antigenic compound sufficient to stimulate an immune response, when administered with a subject immunogenic composition, as compared with the immune response elicited by the antigen in the absence of the additional substance.

As used herein, a "vaccine" is an immunogenic preparation that is used to induce an immune response in an individual. A vaccine can have more than one constituent that is immunogenic. A vaccine can be used for prophylactic and/or therapeutic purposes. A vaccine does not necessarily have to prevent viral infections. Without being bound by theory, the vaccines of the invention can affect an individual's immune response in a manner such that viral infection occurs in a lesser amount (including not at all) or such that biological or physiological effects of the viral infection are ameliorated when the vaccine is administered as described herein.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of infection, stabilized (i.e., not worsening) state of infection, amelioration or palliation of the infectious state, and decrease in viral titer (whether detectable or undetectable). "Treatment" can also mean prolonging survival as compared to expected survival if not receiving treatment. Symptoms of viral infection (such as influenza infection) is known to one of skill in the art and can include, but is not limited to, fever, coughing, runny nose, congestion, muscle aches, wheezing, nausea, and fatigue.

An "effective amount" or a "sufficient amount" of a substance is that amount sufficient to cause a desired biological effect, such as beneficial results, including clinical results, and, as such, an "effective amount" depends upon the context in which it is being applied. In the context of this invention, an example of an effective amount of a vaccine is an amount sufficient to induce an immune response (e.g., antibody production) in an individual. An effective amount can be administered in one or more administrations.

In certain embodiments, the effective amount does not result in complete protection from an influenza virus disease, but results in a lower titer or reduced number of influenza viruses compared to an untreated subject. In certain embodiments, the effective amount results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject. In some embodiments, the effective amount results in a reduction in titer of influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs. Benefits of a reduction in the titer, number or total burden of influenza virus include, but are not limited to, less severe symptoms of the infection, fewer symptoms of the infection and a reduction in the length of the disease associated with the infection.

Fusion Proteins

In the present invention, a first polypeptide encoding a modified influenza HA stem domain and a trimerization domain are joined to form a fusion protein. As used herein, the terms "fusion protein" or "fusion polypeptide" or grammatical equivalents herein is meant a protein composed of a plurality of protein components, which are typically unjoined in their native state but may be joined to form a single continuous polypeptide. The sequence of the HA antigen is modified from the wild-type by the substitution of one or more hydrophobic amino acid residues with polar amino acids, particularly the substitution of hydrophobic residues in the exposed domain with polar amino acids. The sequence is further modified by the deletion of polypeptide regions in the stem containing hydrophobic residues and cysteines. The modified HA antigen is fused to a trimerization domain, including without limitation, T4 bacteriophage fibritin foldon. In some embodiments the sequence is modified to allow the introduction of unnatural amino acids useful in linking the antigen to a virus-like particle (VLP), where a defined unnatural amino acid may be positioned at the terminus of the trimerization domain, or outside of the helical structure of the HA stem. In additional embodiments the sequence is modified to include a motif useful in protein purification, e.g. a histidine tag, a protease cleavage site and the like.

Figure 12:
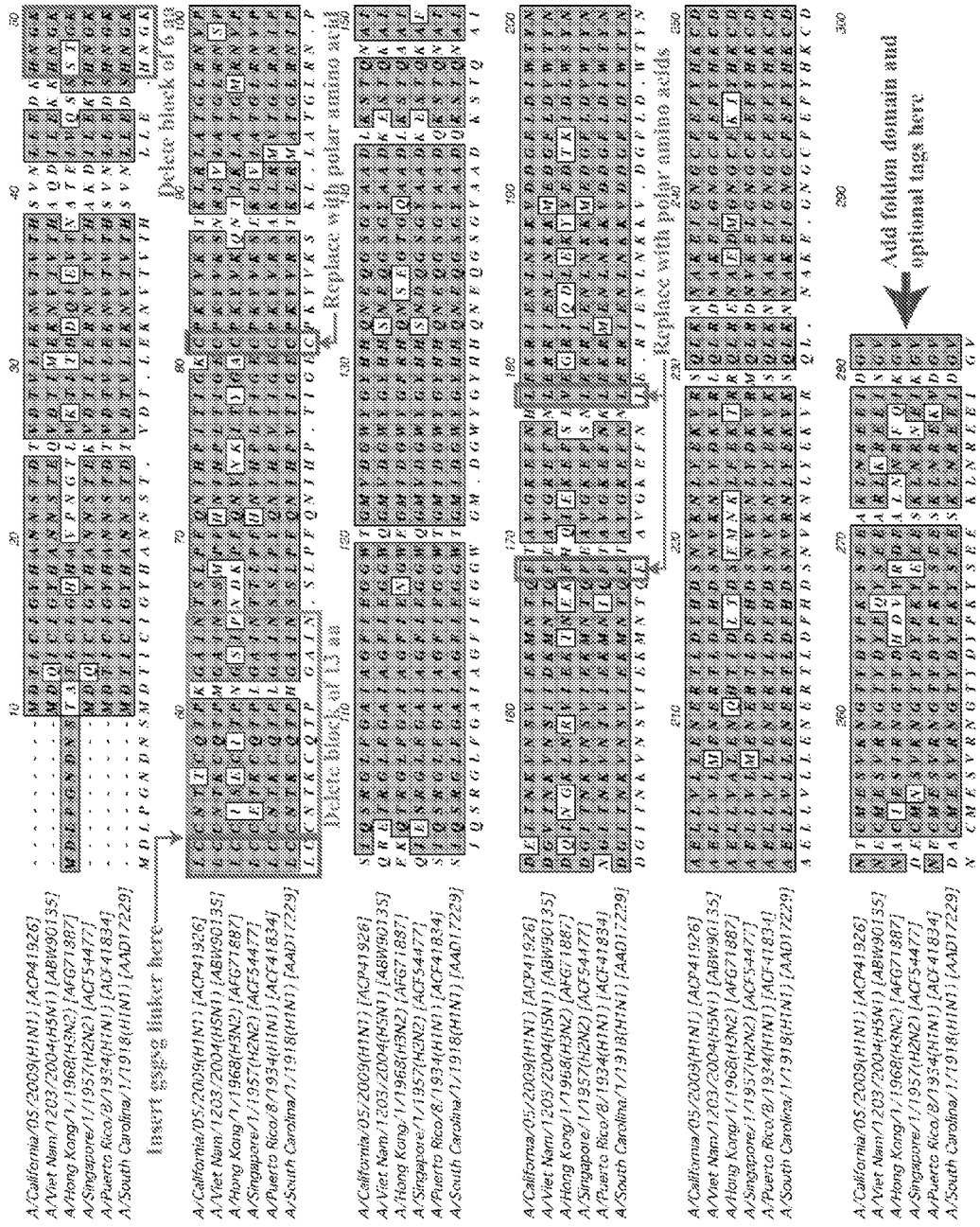
FIG. 12. Summary of amino acid changes.
Figure 13:
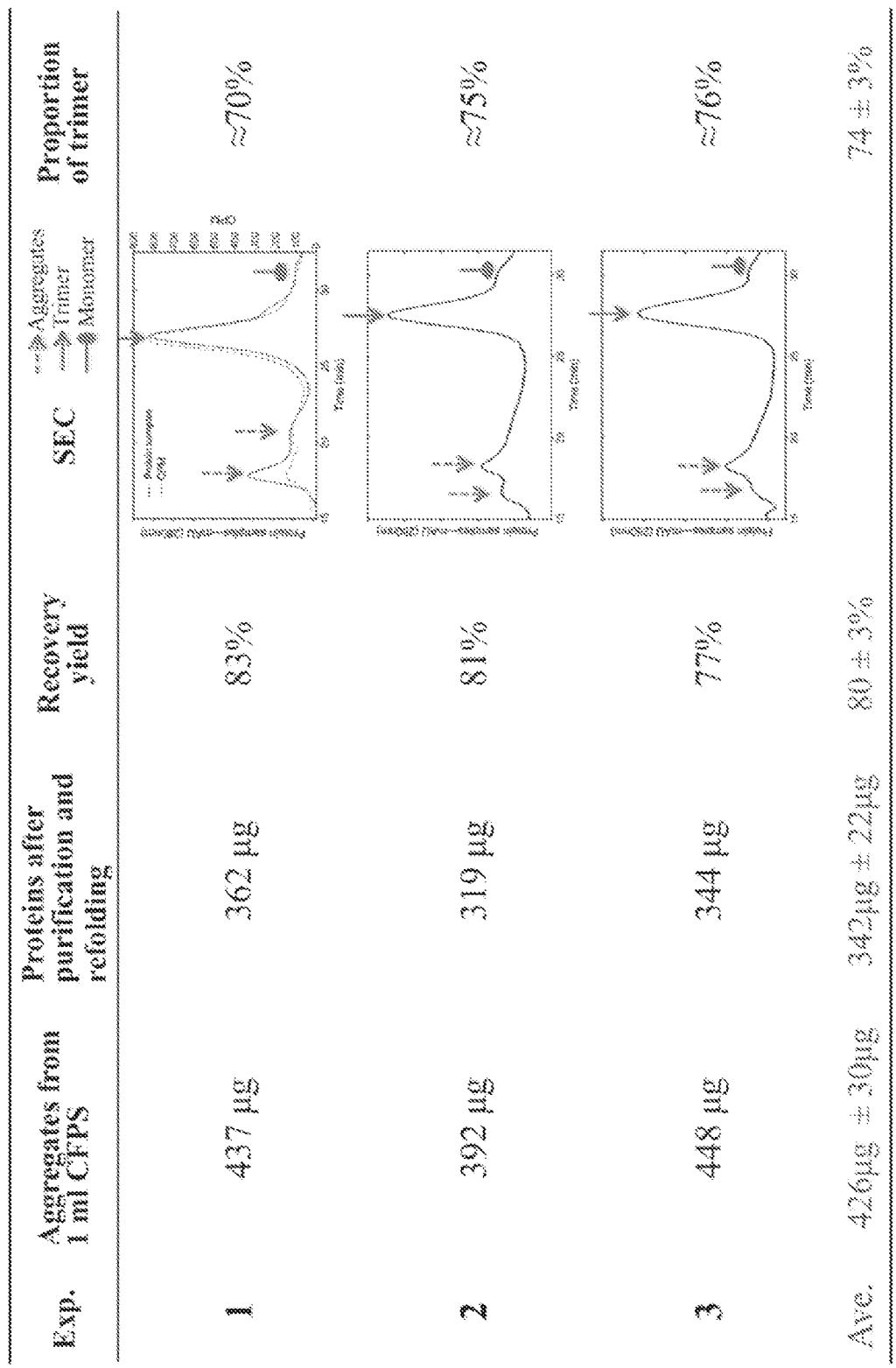
FIG. 13. Triplicate protein refolding experimental results, using mutant M6.

In some embodiments, the polypeptide comprises an amino acid sequence set forth in SEQ ID NO:9, 10, 11, 12, 13, 14 or 15. In some embodiments the polypeptide comprises a modified HA stem polypeptide as illustrated in FIG. 12. A candidate HA stem region may be modified as set forth in FIG. 12. A candidate stem region may be at least about 65% identical to SEQ ID NO:1, at least about 75% identical, at least about 85% identical, at least about 90% identical, or more. A candidate sequence is readily aligned by one of skill in the art to the provided exemplary HA stem domain sequences, and the specific amino acid changes described here and depicted in FIG. 12 made at the indicated positions, e.g. one or more of: insertion of a linker, fusion to a foldon domain, substitution of specific hydrophobic amino acids, deletion of cysteine containing regions and substitution of cysteine residue, including polypeptides in which all of such changes have been made.

While not intending to be bound by any particular theory of operation, it is believed that the influenza hemagglutinin stem domain polypeptides are useful for presenting one or more conserved antigenic regions to a host immune system in order to generate an immune response that is capable of cross-reacting with a plurality of influenza strains. Since the one or more antigenic regions are well conserved across influenza hemagglutinin subtypes, such an immune response might cross-react with several subtypes of full-length influenza hemagglutinin polypeptides. However it has been found that a native HA stem polypeptide aggregates after synthesis and is difficult to refold into a trimeric structure that can be formulated for administration. The present invention provides targeted amino acid changes in the HA stem domain that allow synthesis, refolding and formulation; where the synthesis may be performed in a cell, e.g. by recombinant methods, or in CFPS.

Influenza hemagglutinin stem domain antigens provided herein are useful for administration to generate an immune response against multiple influenza strains. The influenza hemagglutinin stem domain polypeptides generally do not comprise the highly antigenic, variable globular head domains of conventional influenza vaccine polypeptides, and therefore generate a host immune response against multiple influenza strains that carry the relatively conserved epitopes. The influenza hemagglutinin stem domain polypeptides can be useful for generating a host immune response against any one, two, three, four, five, six, seven, eight, nine, ten, eleven, twelve, thirteen, fourteen, fifteen or sixteen known influenza A hemagglutinin subtypes or a later identified influenza A hemagglutinin subtype. The influenza hemagglutinin stem domain polypeptides can also be useful for generating a host immune response against any influenza B hemagglutinin subtype now known or later identified.

Generally, the influenza hemagglutinin stem domain polypeptides provided herein are polypeptides that comprise or consist essentially of a modified stem domain of an influenza hemagglutinin polypeptide, that is, the stem domain is free of sequences associated with the globular head domain of HA. The stem domain of an influenza hemagglutinin polypeptide is the stem domain that is generally recognized by those of skill in the art.

The influenza hemagglutinin stem domain polypeptides comprise the following deletions of hydrophobic and cysteine containing sequences wherein up to 20, 19, 18, 17, 16, 15, 14, 13, 12, 11, 10, 9, 8, 7, 6, 5, 4, 3, 2 or 1 amino acid residues are deleted from either or both of amino acid residues 52 to 68 and residues 288 to 321 (H3 numbering). These influenza hemagglutinin stem domain polypeptides include forms of HA stem domains wherein up to 4 or 2 cysteines from either or both of amino acid residues 56 to 68 and residues 288 to 323 (H3 numbering) are substituted with any other amino acids. These influenza hemagglutinin stem domain polypeptides include forms of HA stem domains wherein up to 10, 9, 8, 7, 6, 5, 4, 3, 2 or 1 hydrophobic amino acid residues from either or both of amino acid residues 304 to 325 and residues 392 to 425 (H3 numbering) are substituted with polar amino acids (Asp, Glu, Gln, Gly, His, Lys, Ser, Thr or Tyr). Further provided are influenza hemagglutinin stem domain polypeptides comprising deleted and altered HA1 N-terminal stem segments.

The HA stem domain is joined at the C-terminus to a trimerization domain, particularly to a foldon domain. The sequences may be joined through a flexible linker, a protease cleavage site, etc. The foldon domain is optionally linked to a tag for purification, e.g. a his tag.

The HA stem domain is joined at the region/terminus to a trimerization domain, particularly to a foldon domain. The sequences may be joined through a flexible linker, a protease cleavage site, etc. The foldon domain is optionally linked to a tag for purification, e.g. a his tag.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like. In some embodiments an unnatural amino acid is included at one or more defined sites in the protein, particularly at the terminus of the foldon domain, or outside of the helical structures of the HA stem domain. The unnatural amino acid may be placed near either the base or the top of the HA stem domain or on the side of the domain. Optimal placement of the attachment site can be determined by testing to see which site of incorporation and which orientation of the HA stem domain on the surface of a VLP or other carrier allows for acceptable conjugation efficiency while eliciting the strongest and/or most effective protective immune responses as determined by standard testing protocols in animal models.

The invention further provides nucleic acids encoding the fusion polypeptides of the invention. As will be appreciated by those in the art, due to the degeneracy of the genetic code, an extremely large number of nucleic acids may be made, all of which encode the fusion proteins of the present invention. Thus, having identified a particular amino acid sequence, those skilled in the art could make any number of different nucleic acids, by simply modifying the sequence of one or more codons in a way that does not change the amino acid sequence of the fusion protein.

Using the nucleic acids of the present invention that encode a fusion protein, a variety of expression constructs can be made. The expression constructs may be self-replicating extrachromosomal vectors or vectors which integrate into a host genome. Alternatively, for purposes of cell-free expression, the construct may include those elements required for transcription and translation of the desired polypeptide but may not include such elements as an origin of replication, selectable marker, etc. Cell-free constructs may be replicated in vitro, e.g. by PCR, and may comprise terminal sequences optimized for amplification reactions.

Generally, expression constructs include transcriptional and translational regulatory nucleic acid operably linked to the nucleic acid encoding the fusion protein. The term "control sequences" refers to DNA sequences necessary for the expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading phase. Linking is accomplished by ligation or through amplification reactions. Synthetic oligonucleotide adaptors or linkers may be used for linking sequences in accordance with conventional practice.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in in vitro expression systems, such as the T7 promoter.

In addition, the expression construct may comprise additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selection genes are well known in the art and will vary with the host cell used.

Cell-Free Synthesis

In some embodiments of the invention, the fusion protein is produced by cell-free, or in vitro synthesis, in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Such synthetic reaction systems are well-known in the art, and have been described in the literature. A number of reaction chemistries for polypeptide synthesis can be used in the methods of the invention. For example, reaction chemistries are described in U.S. Pat. No. 6,337,191, issued Jan. 8, 2002, and U.S. Pat. No. 6,168,931, issued Jan. 2, 2001, herein incorporated by reference.

In one embodiment of the invention, the reaction chemistry is as described in co-pending patent application U.S. Ser. No. 10/643,683, filed Aug. 18, 2003, now issued U.S. Pat. No. 7,338,789, herein incorporated by reference. Oxidative phosphorylation is activated, providing for increased yields and enhanced utilization of energy sources. Improved yield is obtained by a combination of factors, including the use of biological extracts derived from bacteria grown on a glucose containing medium; an absence of polyethylene glycol; and optimized magnesium concentration. This provides for a system homeostatic in [$PO_4$] and pH, in which synthesis can occur even in the absence of secondary energy sources.

The template for cell-free protein synthesis can be either mRNA or DNA. Translation of stabilized mRNA or combined transcription and translation converts stored information into protein. The combined system, generally utilized in E. coli systems, continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Other salts, particularly those that are biologically relevant, such as manganese, may also be added. Potassium is generally added between 50-250 mM and ammonium between 0-100 mM. The pH of the reaction is generally between pH 6 and pH 9. The temperature of the reaction is generally between 20° C. and 40° C. These ranges may be extended.

Metabolic inhibitors to undesirable enzymatic activity may be added to the reaction mixture. Alternatively, enzymes or factors that are responsible for undesirable activity may be removed directly from the extract or the gene encoding the undesirable enzyme may be inactivated or deleted from the chromosome of the extract source cells.

Vesicles, either purified from the host organism or synthetic, may also be added to the system. These may be used to enhance protein synthesis and folding. This cytomim technology has been shown to activate processes that utilize membrane vesicles containing respiratory chain components for the activation of oxidative phosphorylation. The present methods may be used for cell-free expression to activate other sets of membrane proteins.

Synthetic systems of interest include the replication of DNA, which may include amplification of the DNA, the transcription of RNA from DNA or RNA templates, the translation of RNA into polypeptides, and the synthesis of complex carbohydrates from simple sugars.

The reactions may be large scale, small scale, or may be multiplexed to perform a plurality of simultaneous syntheses. Additional reagents may be introduced to prolong the period of time for active synthesis. Synthesized product is usually accumulated in the reactor and then is isolated and purified according to the usual methods for protein purification after completion of the system operation.

Of particular interest is the translation of mRNA to produce proteins, which translation may be coupled to in vitro synthesis of mRNA from a DNA template. Such a cell-free system will contain all factors required for the translation of mRNA, for example ribosomes, amino acids, tRNAs, aminoacyl synthetases, elongation factors and initiation factors. Cell-free systems known in the art include E. coli extracts, etc., which can be treated with a suitable nuclease to eliminate active endogenous mRNA.

In addition to the above components such as cell-free extract, genetic template, and amino acids, materials specifically required for protein synthesis may be added to the reaction. These materials include salts, polymeric compounds, cyclic AMP, inhibitors for protein or nucleic acid degrading enzymes, inhibitors or regulators of protein synthesis, oxidation/reduction adjusters, non-denaturing surfactants, buffer components, putrescine, spermine, spermidine, etc.

The salts preferably include potassium, magnesium, and ammonium salts of acetic acid or sulfuric acid, and some of these may have amino acids as a counter anion. The polymeric compounds may be polyethylene glycol, dextran, diethyl aminoethyl dextran, quaternary aminoethyl and aminoethyl dextran, etc. The oxidation/reduction adjuster may be dithiothreitol, ascorbic acid, glutathione and/or their oxides. Also, a non-denaturing surfactant such as Triton X-100 may be used at a concentration of 0-0.5 M. Spermine and spermidine or optionally, in combination, putrescine may be used for improving protein synthetic ability, and cAMP may be used as a gene expression regulator.

When changing the concentration of a particular component of the reaction medium, that of another component may be changed accordingly. For example, the concentrations of several components such as nucleotides and energy source compounds may be simultaneously controlled in accordance with the change in those of other components. Also, the concentration levels of components in the reactor may be varied over time.

Preferably, the reaction is maintained in the range of pH 5-10 and a temperature of 20°-50° C., and more preferably, in the range of pH 6-9 and a temperature of 25°-40° C.

The amount of protein produced in a translation reaction can be measured in various fashions. One method relies on the availability of an assay which measures the activity of the particular protein being translated. Examples of assays for measuring protein activity are a luciferase assay system, and a chloramphenical acetyl transferase assay system. These assays measure the amount of functionally active protein produced from the translation reaction. Activity assays will not measure full-length protein that is inactive due to improper protein folding or lack of other post translational modifications necessary for protein activity.

Another method of measuring the amount of protein produced in a combined in vitro transcription and translation reactions is to perform the reactions using a known quantity of radiolabeled amino acid such as $^{35}$S-methionine or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

Formulations and Uses

The compositions of the invention comprise any of the polypeptide populations described herein can be formulated in a sufficient amount to modulate an immune response. Such a formulation can be used as a therapeutic or prophylatic in the treatment of influenza virus infection. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}ED_{50}$. Compounds that exhibit large therapeutic indices are preferred.

The data obtained from cell culture assays and animal studies can be used in formulating a range of dosage for use in humans. The dosage of such compounds lies preferably within a range of circulating concentrations that includes the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that provides a booster stimulus to generate a rapid viral neutralizing response as determined using standard testing protocols in animals. Such information can be used to more accurately determine useful doses in humans. Levels of the elicited antibodies in plasma may be measured, for example, by standard Elisa type assays or using other assay formats. In some cases, the HA stem protein by be fused to other polypeptides or may be co-administered with immune response stimulators to provide a more rapid and effective therapeutic response.

The compounds of the invention may, further, serve the role of a prophylactic vaccine, wherein the host produces antibodies and/or CTL responses against influenza virus HA protein, which responses then serve to neutralize influenza viruses by, for example, inhibiting further influenza infection. Administration of the compounds of the invention as a prophylactic vaccine comprise administering to a host a concentration of antigenic compounds effective in raising an immune response sufficient to elicit antibody and/or CTL responses to influenza virus HA protein, and/or neutralize an influenza virus, by, for example, inhibiting the ability of the virus to infect cells. The exact concentration will depend upon the specific compound to be administered, but may be determined by using standard techniques for assaying the development of an immune response which are well known to those of ordinary skill in the art.

The compounds may be formulated with a suitable adjuvant in order to enhance the immunological response. Such adjuvants may include, but are not limited to mineral gels such as aluminum hydroxide; surface active substances such as lysolecithin, pluronic polyols, polyanions; other peptides; oil emulsions; and potentially useful human adjuvants such as BCG and *Corynebacterium parvum*.

Adjuvants suitable for co-administration in accordance with the present invention should be ones that are potentially safe, well tolerated and effective in people including QS-21, Detox-PC, MPL-SE, MoGM-CSF, TiterMax-G, CRL-1005, GERBU, TERamide, PSC97B, Adjumer, PG-026, GSK-1, GcMAF, B-alethine, MPC-026, Adjuvax, CpG ODN, Betafectin, Alum, and MF59 (see Kim et al., 2000, Vaccine, 18: 597 and references therein).

For all such treatments described above, the exact formulation, route of administration and dosage can be chosen by the individual physician in view of the patient's condition. (See e.g., Fingl et al., 1975, in "The Pharmacological Basis of Therapeutics"). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administered dose in the management of the viral infection of interest will vary with the severity of the condition to be treated and the route of administration. The dose and perhaps prime-boost regimen, will also vary according to the age, weight, and response of the individual patient. A program comparable to that discussed above may be used in veterinary medicine.

The pharmacologically active compounds of this invention can be processed in accordance with conventional methods of pharmaceutical formulation to produce medicinal agents for administration to patients, e.g., mammals including humans.

Generally, the compositions of the invention preferably also comprise a pharmaceutically acceptable excipient, and may be in various formulations. As is well known in the art, a pharmaceutically acceptable excipient is a relatively inert substance that stabilizes and facilitates administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington's Pharmaceutical Sciences 19th Ed. Mack Publishing (1995).

Other formulations include suitable delivery forms known in the art including, but not limited to, carriers such as liposomes. Mahato et al. (1997) Pharm. Res. 14:853-859. Liposomal preparations include, but are not limited to, cytofectins, multilamellar vesicles and unilamellar vesicles.

Generally, these compositions are formulated for administration by injection or inhalation, e.g., intraperitoneally, intravenously, subcutaneously, intradermally, intramuscularly, etc. Accordingly, these compositions may be combined with pharmaceutically acceptable vehicles such as saline, Ringer's solution, dextrose solution, and the like. The particular dosage regimen, i.e., dose, timing and repetition, will depend on the particular individual and that individual's medical history.

In some embodiments, more than one antigen(s) may be present in a composition. Such compositions may contain at least one, at least two, at least three, at least four, at least five, or more different antigen(s). Such "cocktails", as they are often denoted in the art, may be particularly useful in immunizing against pathogens present in different variants.

Generally, the efficacy of administering any of these compositions is adjusted by measuring any change in the immune response as described herein, or other clinical parameters.

In some embodiments, the antigenic compounds described herein can be administered in conjunction with one or more immunomodulatory facilitators. Thus, the invention provides compositions comprising fusion protein populations, VLPS, etc., and an immunomodulatory facilitator. As used herein, the term "immunomodulatory facilitator" refers to molecules which support and/or enhance the immunomodulatory activity of an immunity protein linker. Examples of immunomodulatory facilitators can include co-stimulatory molecules, such as cytokines, toll-like receptor agonists, and/or adjuvants. The association of the linker and the facilitator molecules in a linker-facilitator conjugate can be through covalent interactions and/or through non-covalent interactions, including high affinity and/or low affinity interactions. Examples of non-covalent interactions that can couple an immunity protein linker and a facilitator include, but are not limited to, ionic bonds, hydrophobic interactions, hydrogen bonds and van der Waals attractions.

Immunomodulatory facilitators include, but are not limited to, co-stimulatory molecules (such as cytokines, chemokines, DNA sequences, targeting protein ligand, trans-activating factors, peptides, and peptides comprising a modified amino acid), adjuvants (such as alum, lipid emulsions, etc.).

Among suitable immunomodulatory cytokine peptides for administration with linker are the interleukins (e.g., IL-1, IL-2, IL-3, etc.), interferons (e.g., IFN-α, IFN-β, IFN-γ), colony stimulating factors (e.g., G-CSF, M-CSF, GM-CSF) and TNF-α. Preferably, immunostimulatory peptides for use in conjunction with linker oligonucleotides are those that stimulate Th1-type immune responses, such as IL-12 (Bliss et al. (1996) J. Immunol. 156:887-894), IL-15, IL-18, TNF-α, β and γ, and/or transforming growth factor (TGF)-α.

The invention also provides compositions which comprise antigenic compositions in conjunction with colloidal dispersion systems, such as microspheres, beads, macromolecular complexes, nanocapsules and lipid-based system, such as oil-in-water emulsions, micelles, mixed micelles and liposomes. Colloidal dispersion systems can provide effective encapsulation of linker-containing compositions. The encapsulation composition further comprises any of a wide variety of components. These include, but are not limited to, alum, lipids, phospholipids, lipid membrane structures (LMS), polyethylene glycol (PEG) and other polymers, such as polypeptides, glycopeptides, polylactide/polyglycolide copolymers, and polysaccharides.

As with all immunogenic compositions, the immunologically effective amounts and method of administration of the particular antigenic formulation can vary based on the individual, what condition is to be treated and other factors evident to one skilled in the art. Factors to be considered include the antigenicity, whether or not the composition will be complexed with or covalently attached to an adjuvant or delivery molecule, route of administration and the number of immunizing doses to be administered. Such factors are known in the art and it is well within the skill of immunologists to make such determinations without undue experimentation. A suitable dosage range is one that provides the desired modulation of immune response to the antigen. Generally, a dosage range of the antigen composition may be, for example, from about any of the following: 0.01 to 100 µg, 0.01 to 50 µg, 0.01 to 25 µg, 0.01 to 10 µg, 1 to 500 µg, 100 to 400 µg, 200 to 300 µg, 1 to 100 µg, 100 to 200 µg, 300 to 400 µg, 400 to 500 µg. Alternatively, the doses can be about any of the following: 0.1 µg, 0.25 µg, 0.5 µg, 1.0 µg, 2.0 µg, 5.0 µg, 10 µg, 25 µg, 50 µg, 75 µg, 100 µg. Accordingly, dose ranges can be those with a lower limit about any of the following: 0.1 µg, 0.25 µg, 0.5 µg and 1.0 µg; and with an upper limit of about any of the following: 250 µg, 500 µg and 1000 µg. In these compositions, the molar ratio of immunity protein linker to antigen may vary.

The absolute amount given to each patient depends on pharmacological properties such as bioavailability, clearance rate and route of administration and may also depend on the recipient's age and/or status of the individual's immune system.

Analysis (both qualitative and quantitative) of the immune response to an antigen can be by any method known in the art, including, but not limited to, measuring antigen-specific antibody production (including measuring specific antibody subclasses), activation of specific populations of lymphocytes such as CD4+ T cells or NK cells, production of cytokines such as IFNγ, IL-2, IL-4, IL-5, IL-10 or IL-12 and/or release of histamine. Methods for measuring specific antibody responses include enzyme-linked immunosorbent assay (ELISA) and are well known in the art. Measurement of numbers of specific types of lymphocytes such as CD4+ T cells can be achieved, for example, with fluorescence-activated cell sorting (FACS). Serum concentrations of cytokines can be measured, for example, by ELISA. These and other assays to evaluate the immune response to an immunogen are well known in the art. See, for example, Selected Methods in Cellular Immunology (1980) Mishell and Shiigi, eds., W.H. Freeman and Co.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the reagents, cells, constructs, and methodologies that are described in the publications, and which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

We describe a novel influenza vaccine antigen which is based on a conserved stem region of the HA protein from influenza A virus A/California/05/2009 (H1N1), GenBank accession No. ACP41926). The sequence of HA stem domain from influenza A virus A/California/05/2009 (H1N1) (accession No. ACP41926) was aligned to that of the HA stem domain from five other influenza A viruses, A/Viet Nam/1203/2004(H5N1) (accession No. ABW90135), A/Hong Kong/1/1968(H3N2) (accession No. AFG71887), A/Singapore/1/1957(H2N2) (accession No. ACF54477), A/Puerto Rico/8/1934(H1N1) (accession No. ACF41834), and A/South Carolina/1/1918(H1N1) (accession No. AAD17229), as shown in FIG. 1. The stem domain is very conserved.

Figure 2:
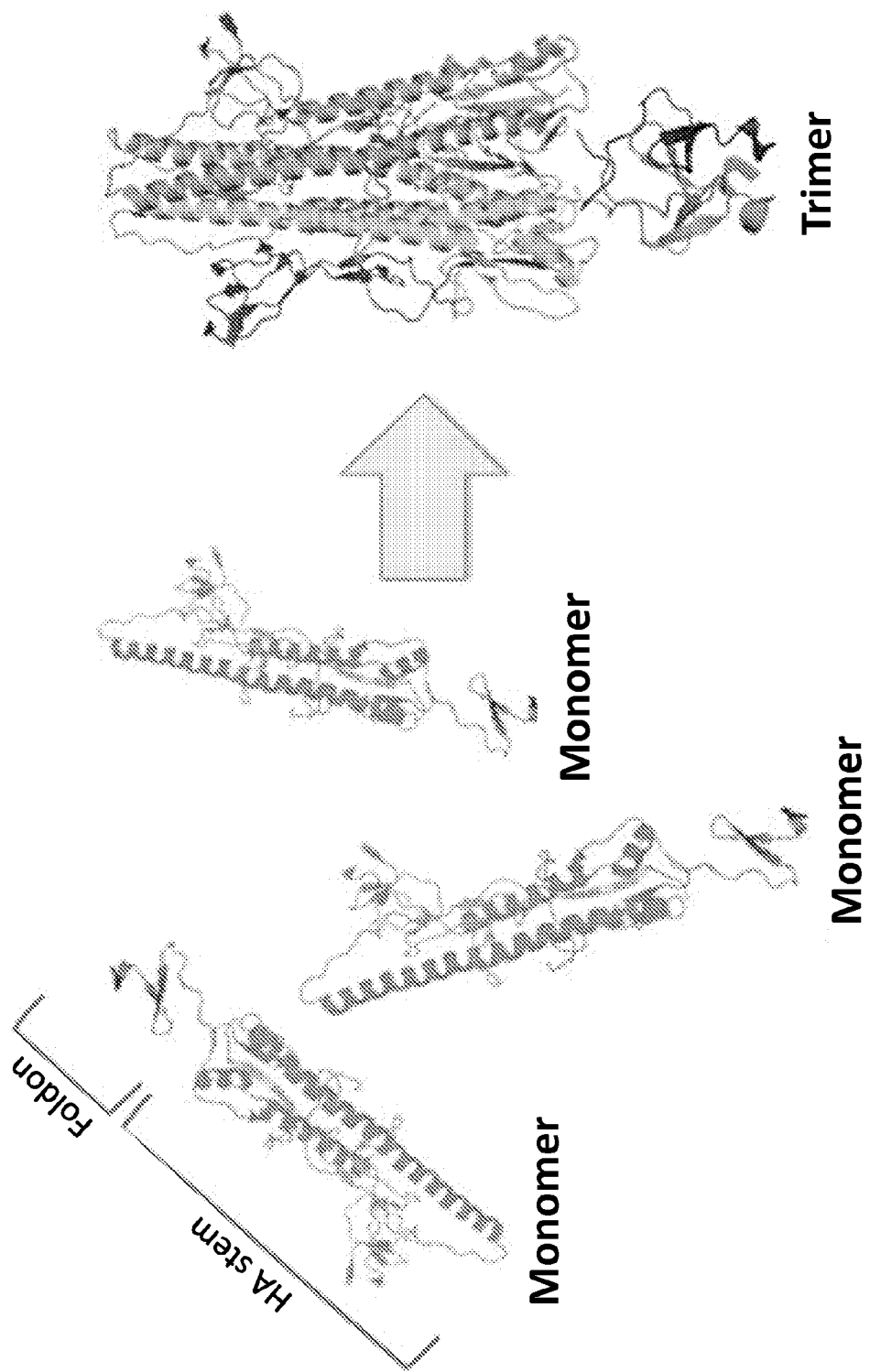
FIG. 2. Trimerization of HA stem domain.
Figure 3:
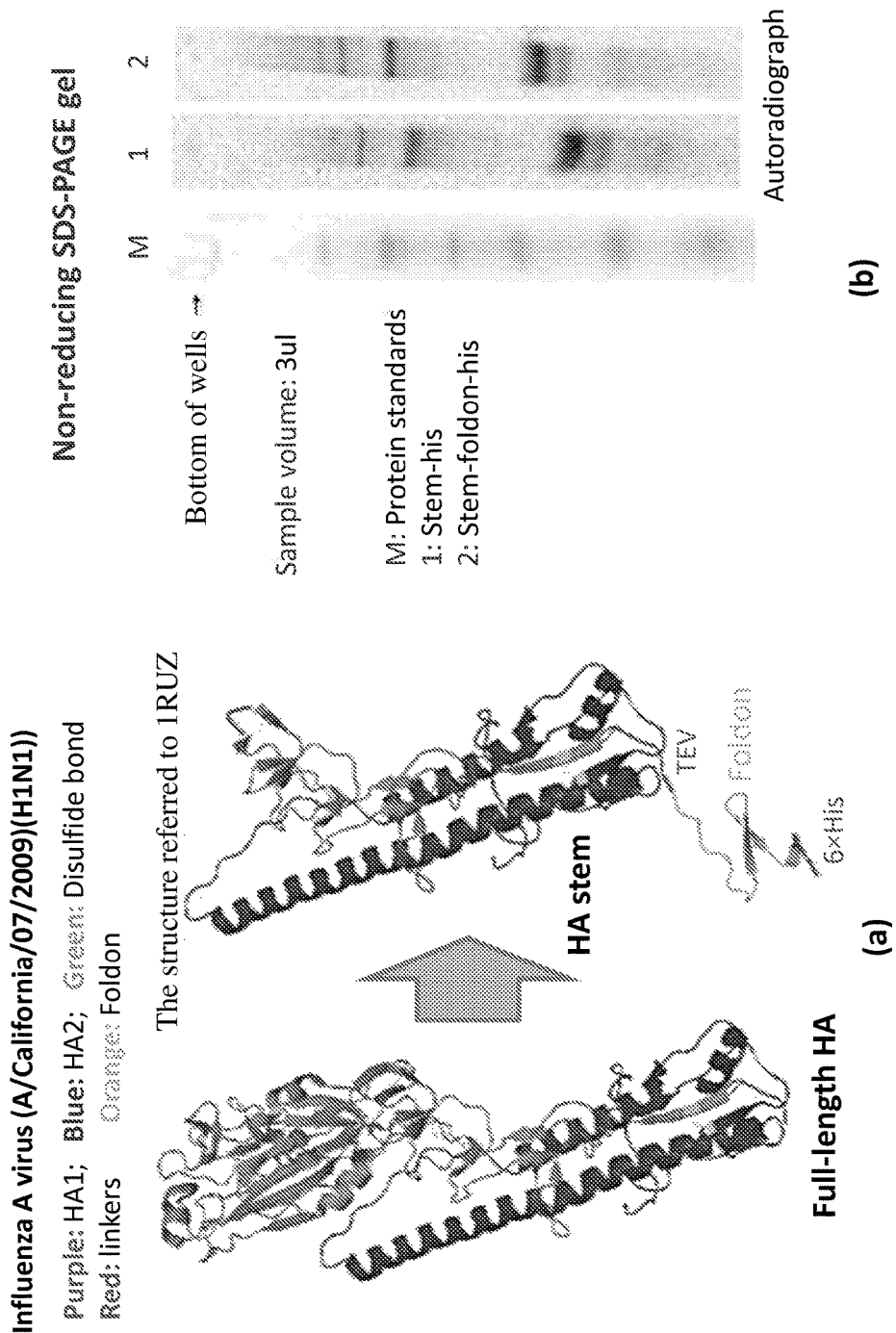
FIG. 3. Initial design of HA stem antigen (a), and initial SDS-PAGE results after protein refolding (b).

The antigen is composed of a fusion between the HA stem domain and a C-terminal 29 amino acid 'foldon' sequence. The foldon was used to induce trimerization (FIG. 2). The foldon domain was separated from the HA stem sequence by an optional cleavable TEV protease site and also contains an optional $His_6$ tag at the C-terminus, as shown in FIG. 3 (a). After protein synthesis and refolding, the SDS-PAGE gel results showed that proteins aggregated, as shown by the higher molecular weight bands in FIG. 3 (b). Incorrect intermolecular disulfide bonds were formed. Size exclusion chromatography also indicated very little trimer formation.

Figure 4:
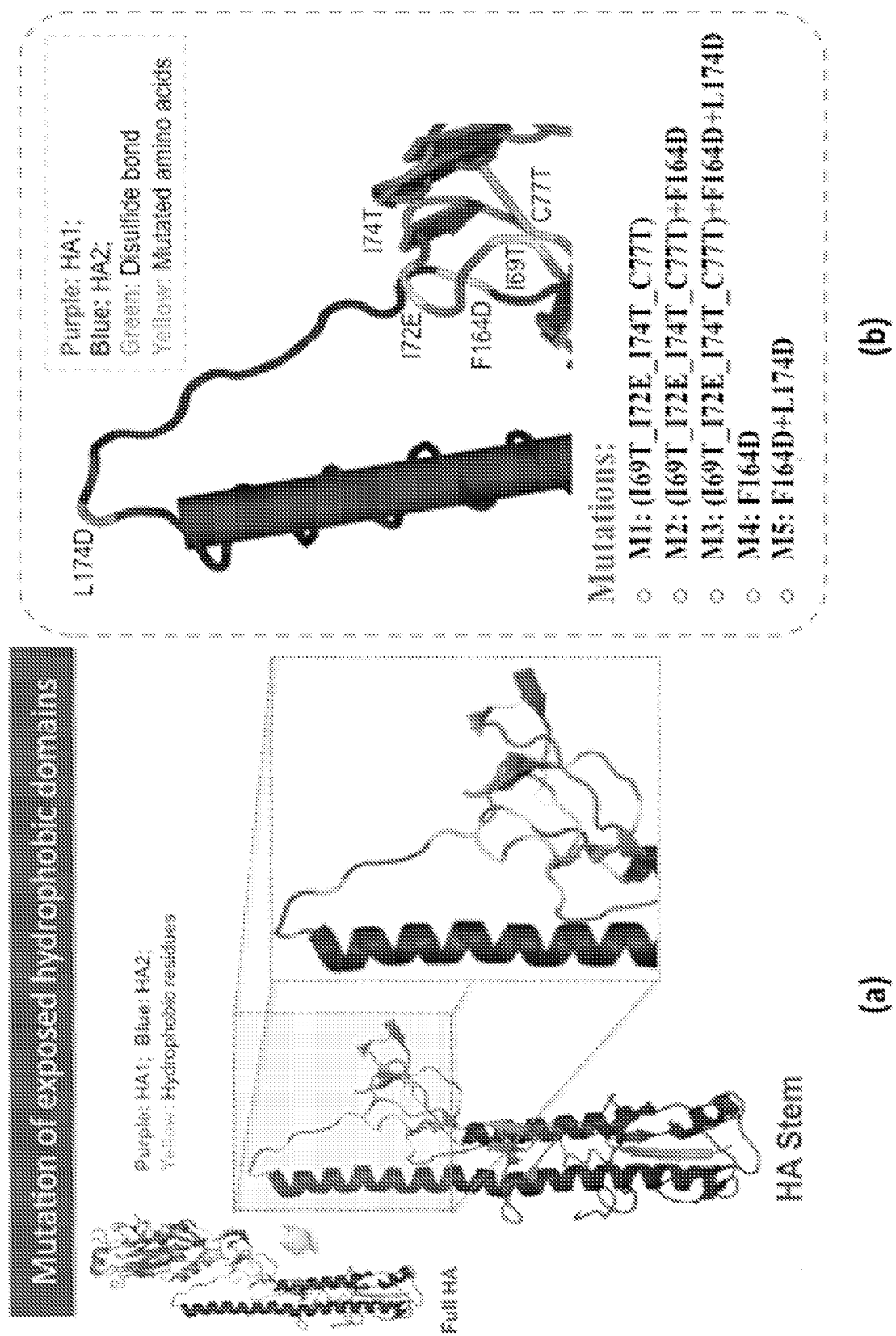
FIG. 4. Exposed hydrophobic regions in HA stem domain (a), and 5 groups of mutated hydrophobic residues (b).
Figure 5:
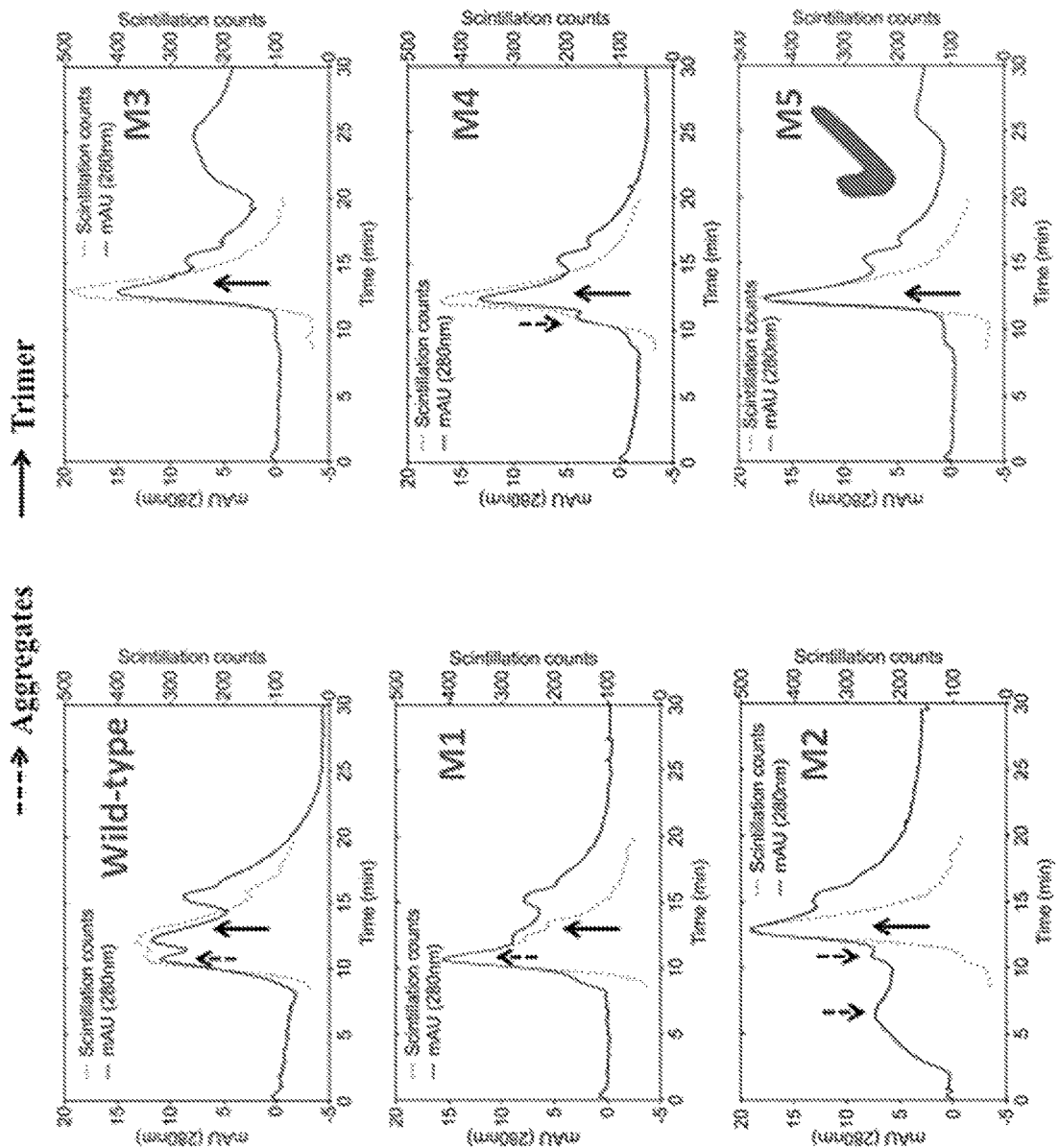
FIG. 5. Size-exclusion HPLC to assess trimerization of 5 different mutated HA stem proteins.

To reduce the chance of aggregation, some exposed hydrophobic residues in the stem domain were mutated. As shown in FIG. 4 (a), the hydrophobic residues come in close contact with the head domain in the full-length ectodomain structure but are probably exposed when the stem domain is expressed alone. We tried five different groups of mutations, as shown in FIG. 4 (b). The proteins were refolded using Procedure I. To determine if the mutated proteins folded and trimerized better than the wild-type, the purified and refolded mutated proteins were compared to the wild-type protein using size-exclusion HPLC (FIG. 5). The results showed that mutants M3 and M5 formed less aggregates. M5 had fewer mutations than M3 (as shown in FIG. 4 (b)), and also appeared to fold somewhat higher amounts of trimer relative to other species. Therefore, we chose M5 for further studies.

The protein refolding conditions were next re-optimized by orthogonal experimental design, to find the best refolding conditions for the HA stem protein. The proteins were refolded using Procedure II. In the orthogonal experimental design, there were 7 factors and 2 levels (Table 1). We used the $L_8(2^7)$ orthogonal array for this design. The statistical analysis was performed using IBM SPSS software. Table 2 shows the statistical analysis results. Higher mean values indicate that this condition was favorable for the formation of trimers. Inclusion of the detergent Brij 35 was the most beneficial factor for the formation of trimers.

TABLE 2

Statistical analysis results of the orthogonal experiment design

| Source | Mean Square | Most Important Factor |
| --- | --- | --- |
| Buffer | 426.466 | |
| Brij35 | 2565.787 | ✓ |
| Arginine | 356.045 | |
| NaCl | 167.903 | |
| Sucrose | 482.828 | |
| Glycerol | 434.388 | |
| Urea | 202.508 | |

Figure 6:
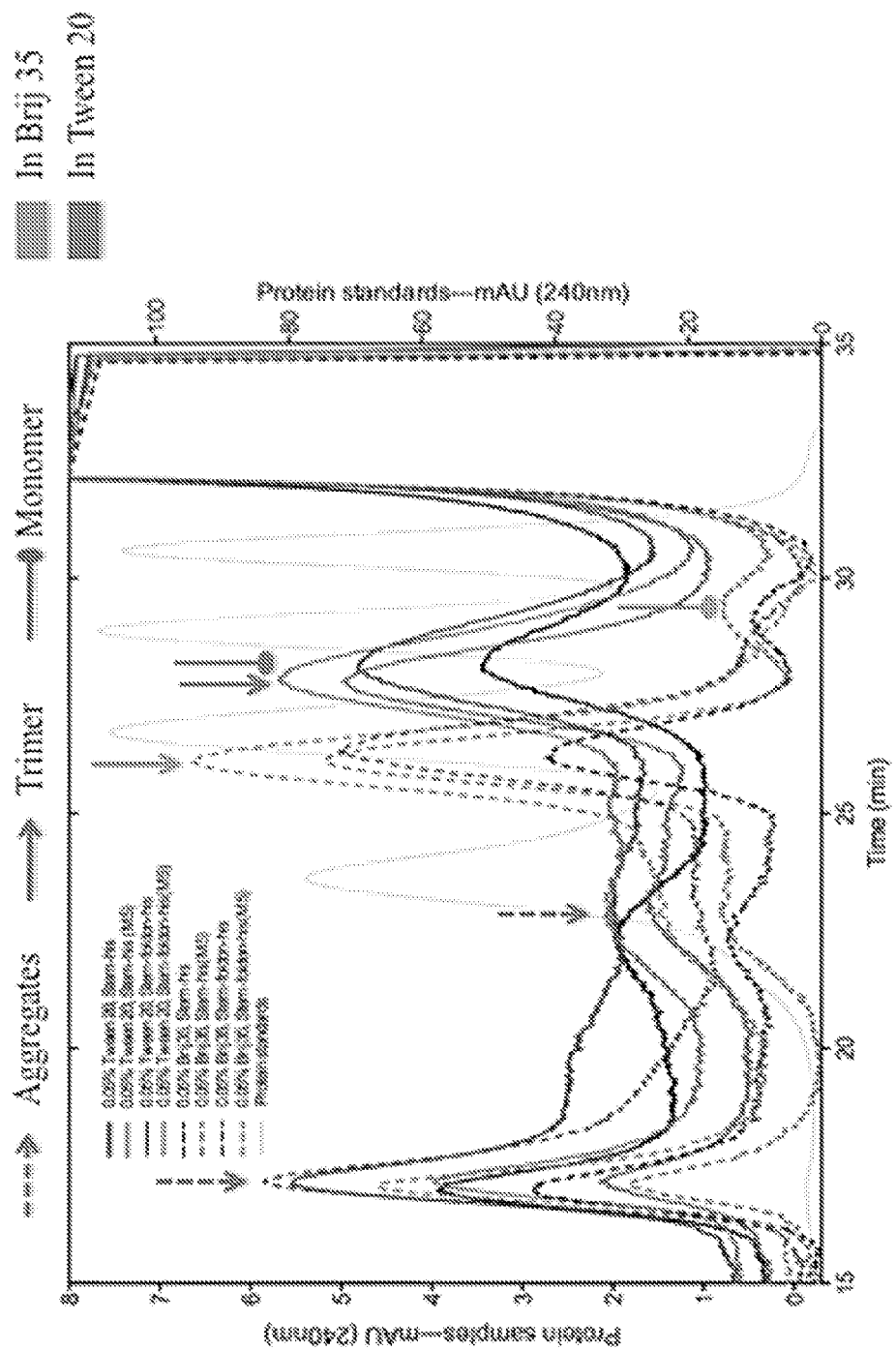
FIG. 6. Effects of detergents on the separation of trimer and monomer in size-exclusion HPLC. The chromatograms also confirm the benefits of the M5 mutations.

Since detergent was very important for the trimer formation. We compared detergent Brij 35 and Tween 20 in size-exclusion HPLC (FIG. 6). The proteins were refolded using Procedure III. The trimer and monomer can be separated better by using Brij 35 than Tween 20 in the running buffer.

Figure 7:
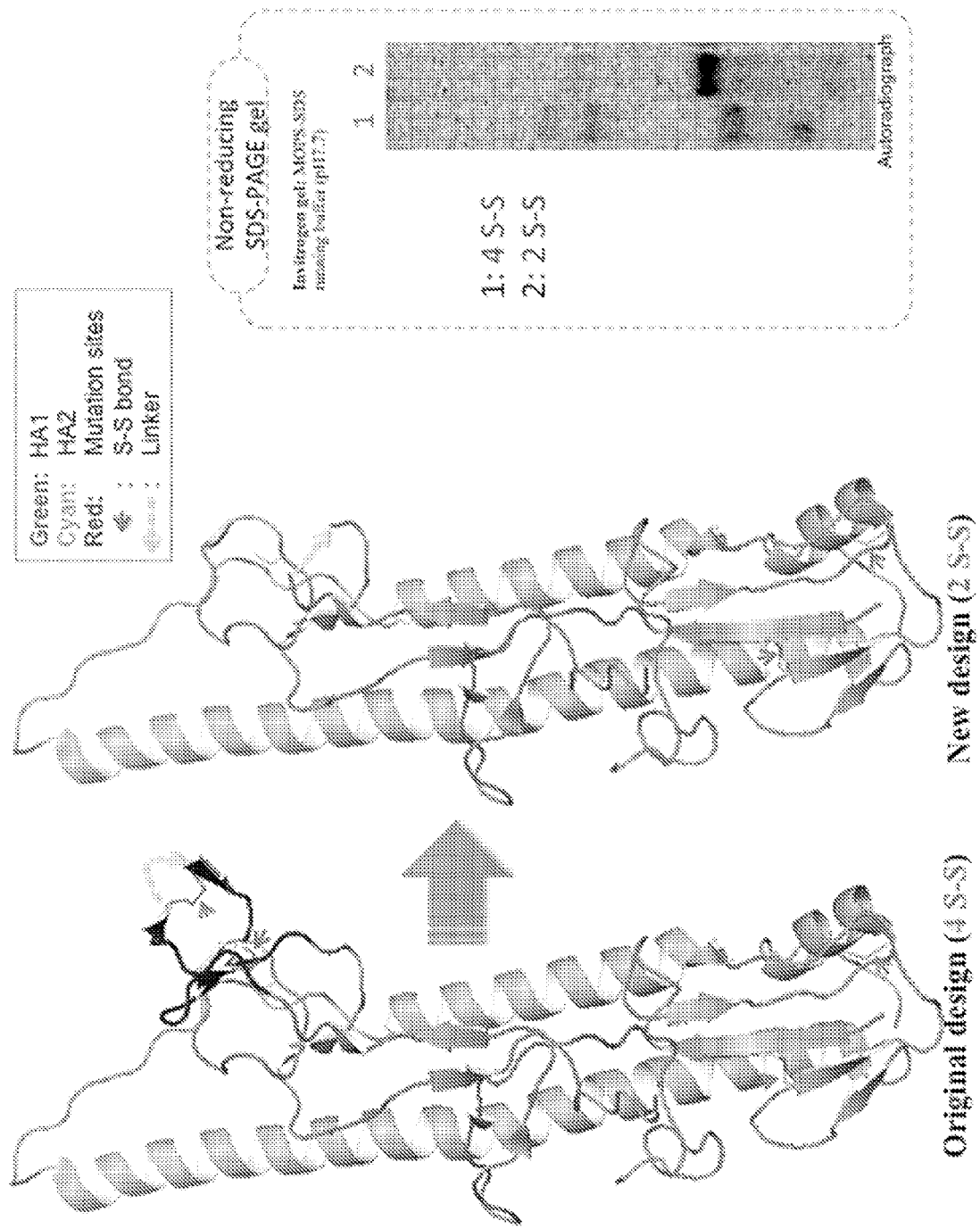
FIG. 7. Effects of disulfide bond numbers on the protein refolding.

To reduce the formation of undesired intermolecular S—S bonds, two polypeptide regions (H38 to C43 and C49 to N61) containing hydrophobic residues and three cysteines were deleted, and cysteine 77 was mutated to threonine (FIG. 7). The number of disulfide bonds in each monomer was thereby reduced from 4 to 2. The new mutant was named as M6. The proteins were refolded using Procedure IV. The SDS-PAGE results showed that the two deletions decreased the formation of undesirable intermolecular S—S bonds.

Figure 8:
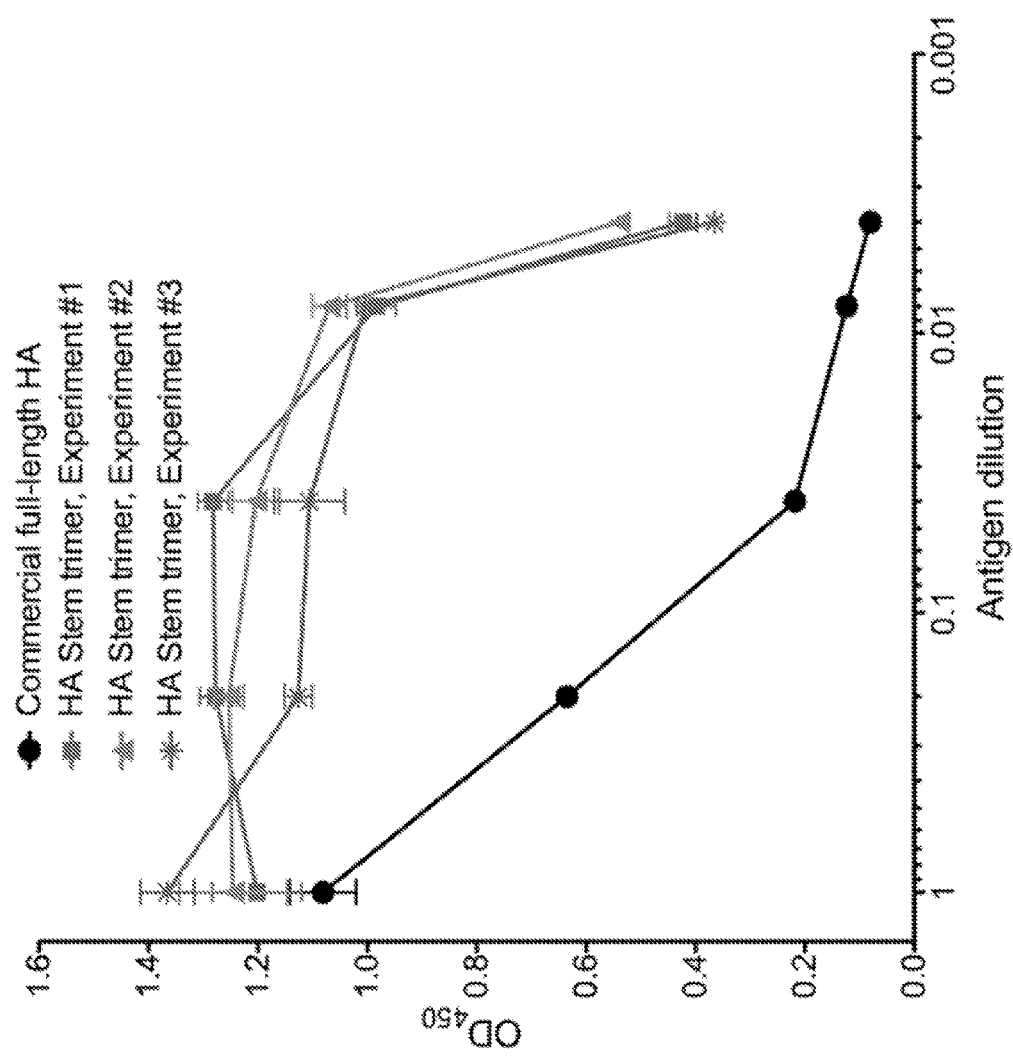
FIG. 8. ELISA analysis of HA stem construct by using antibody C179.

Triplicate experimental results showed that recovery yield could reach around 80% after protein purification and refolding using Procedure IV. The proportion of trimer was around 74% and the results were reproducible in three separate preparations (Table 3). To further confirm the proper conformation of the stabilized HA stem domain trimer, the mutant M6 was compared with commercial full-length HA for their recognition by a commercial antibody (C179) that blocks influenza infection by binding to the HA stem trimer (FIG. 8). The ELISA results showed that the HA stem trimer we constructed was much better recognized by the neutralizing antibody C179 (by approximately 30-fold).

Virus-like particles (VLPs) are non-infectious protein structures that self-assemble into either icosahedral or rod-like structures and are comprised of the coat proteins of viruses. The repeated surface epitopes of VLPs can elicit strong antibody responses, and the size of VLPs, typically 25-100 nm, makes them ideal for trafficking to the lymphatic system to induce T-cell responses. Thus, the immunogenic properties of VLPs have made them an attractive target as the core of effective vaccines. In the cell-free protein synthesis (CFPS) system, non-natural amino acids (nnAAs) can

TABLE 1

Orthogonal experiment design: $L_8(2^7)$ array

Figure 9:
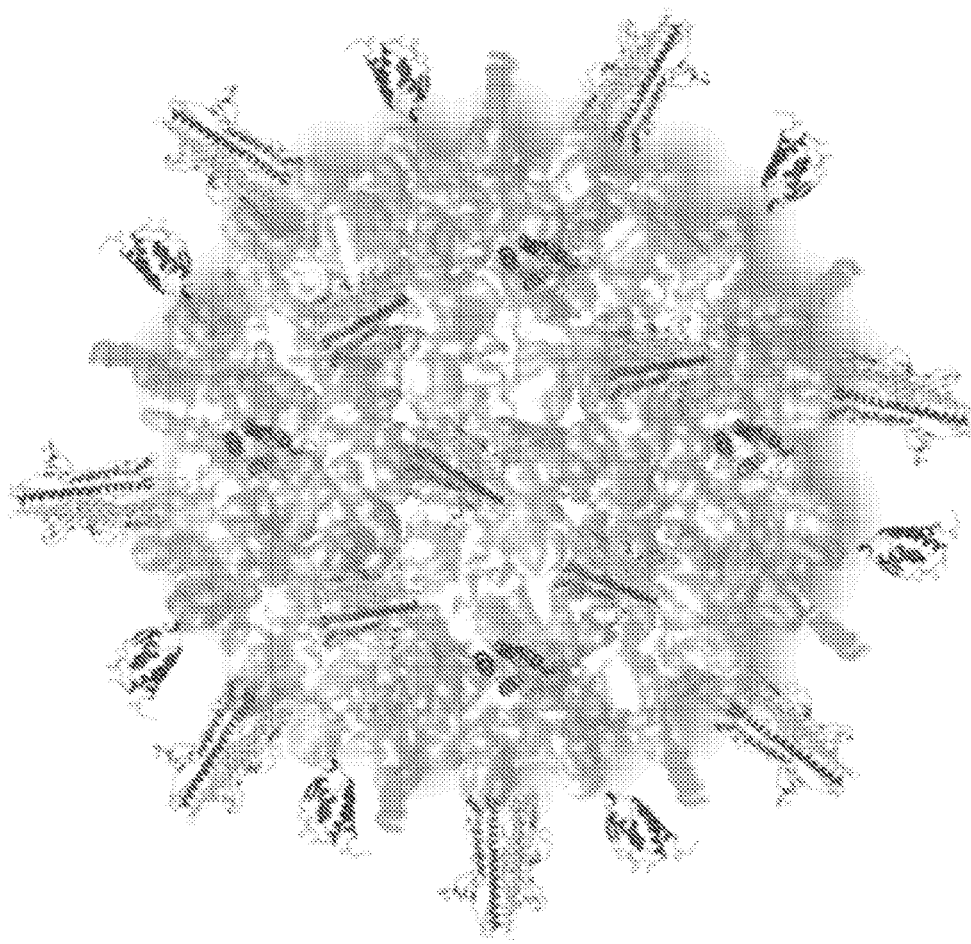
FIG. 9. Assembly of VLP-based vaccines.
Figure 9:
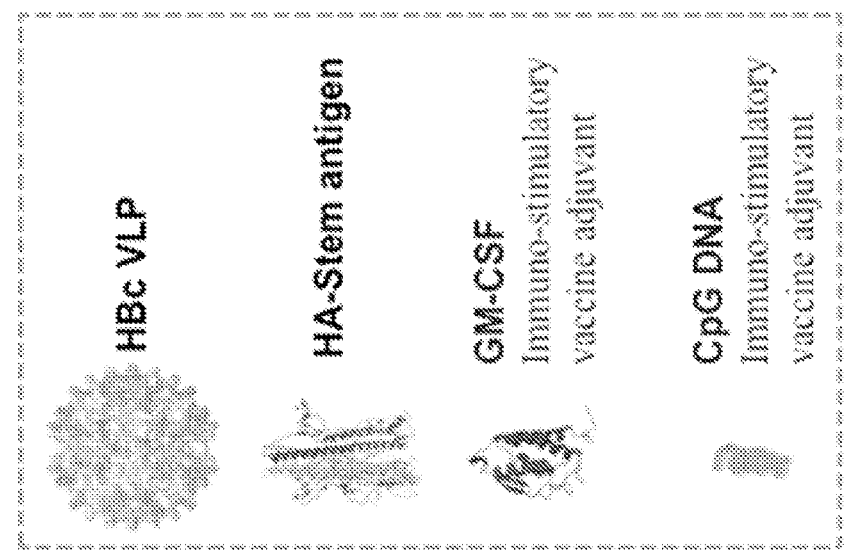

| Factors | 1<br>50 mM Buffer | 2<br>Brij35 | 3<br>Arginine | 4<br>NaCl | 5<br>Sucrose | 6<br>Glycerol | 7<br>Urea | Formed trimers |
| --- | --- | --- | --- | --- | --- | --- | --- | --- |
| Experiment 1 | Tris | 0.00% | 0 mM | 0 mM | 0% | 0% | 0 mM | |
| Experiment 2 | Tris | 0.00% | 0 mM | 150 mM | 10% | 10% | 0.5 mM | |
| Experiment 3 | Tris | 0.03% | 500 mM | 0 mM | 0% | 10% | 0.5 mM | |
| Experiment 4 | Tris | 0.03% | 500 mM | 150 mM | 10% | 0% | 0 mM | |
| Experiment 5 | Histidine | 0.00% | 500 mM | 0 mM | 10% | 0% | 0.5 mM | |
| Experiment 6 | Histidine | 0.00% | 500 mM | 150 mM | 0% | 10% | 0 mM | |
| Experiment 7 | Histidine | 0.03% | 0 mM | 0 mM | 10% | 10% | 0 mM | |
| Experiment 8 | Histidine | 0.03% | 0 mM | 150 mM | 0% | 0% | 0.5 mM | | be incorporated into CFPS produced protein. A nnAA with an alkyne group (p-propargyloxy-phenylalanine) and a nnAA with an azide group (homopropargylglycine) were respectively incorporated into the new HA stem antigen and a VLP surface site on the Hepatitis B core protein (HBc) VLP. The HA stem antigen was then attached to the HBc VLP by a click reaction. Besides the HA stem antigen, other immunostimulatory species like flagellin, GM-CSF and CpG DNA also could be attached to the surface of the same VLP, as shown in FIG. 9.

Figure 10:
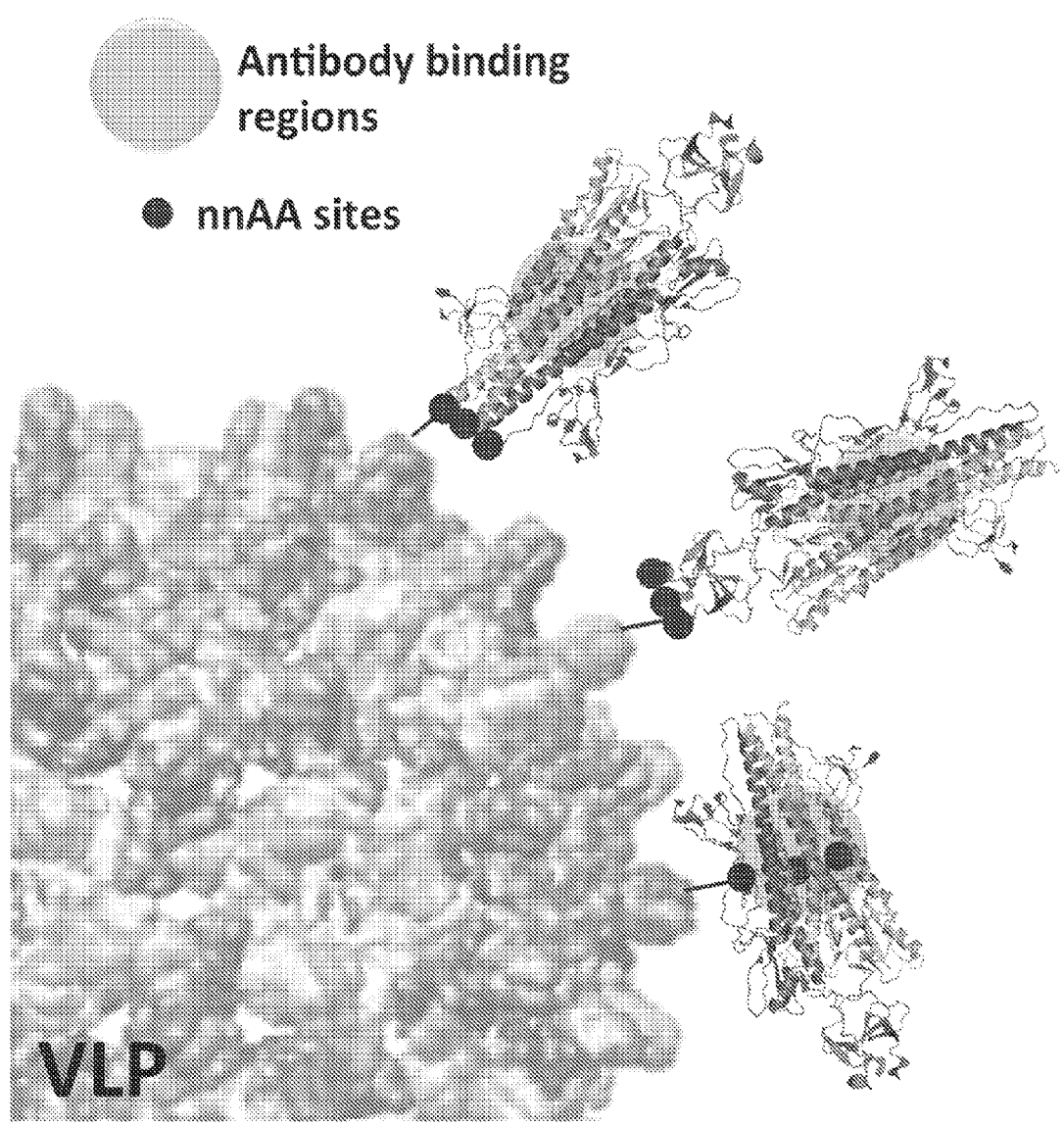
FIG. 10. Design of nnAA sites.
Figure 11:
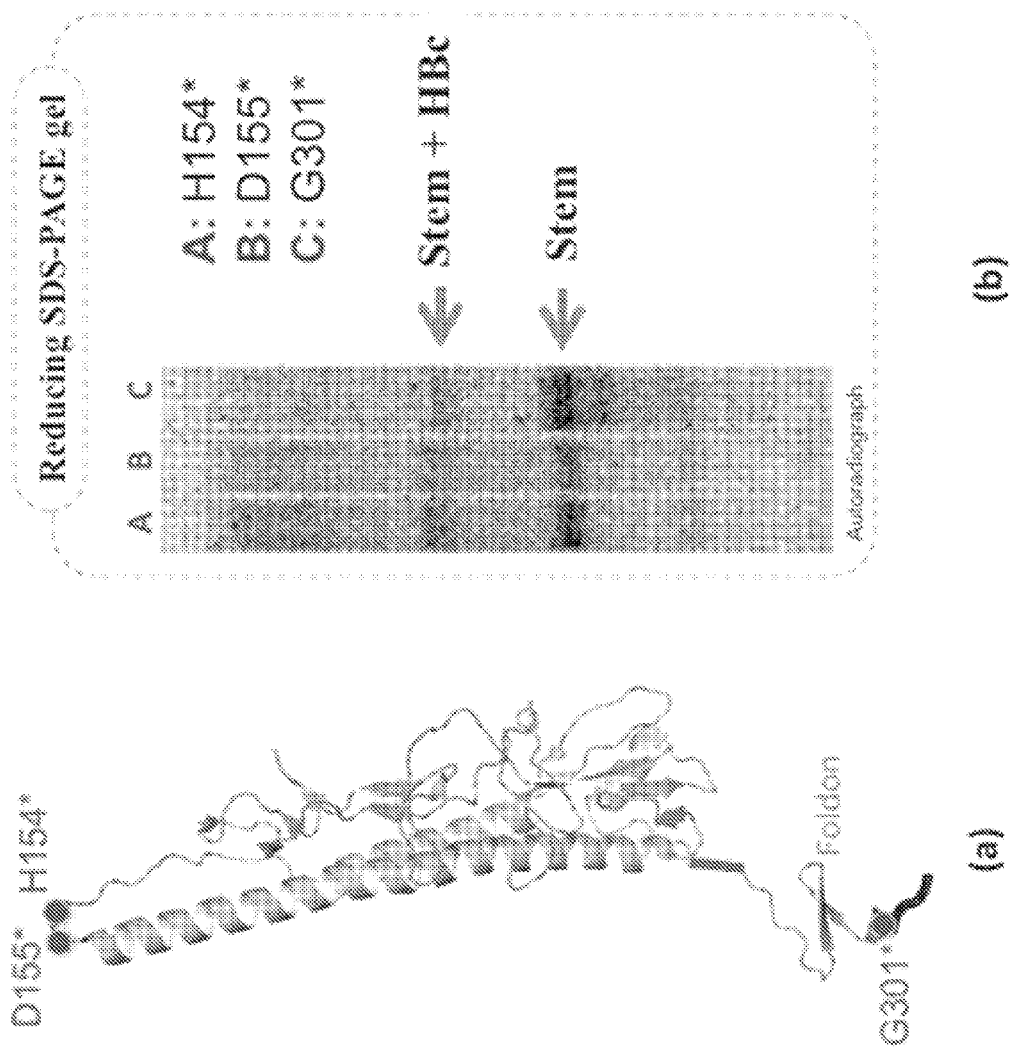
FIG. 11. Attachment of HA stem trimers to HBc-VLPs after click reactions showing the use of three different attachment positions on the HA stem fusion protein.

The primary regions for antibody binding are in the middle of HA stem domain, so nnAAs could be incorporated into the top, middle or bottom of HA stem domain (FIG. 10). For site-specific incorporation of nnAAs into the HA stem, 3 different sites at the top (H154 and D155) and the bottom (G301) of the HA stem construct were chosen (FIG. 11 (a)). The reducing SDS-PAGE results (FIG. 11 (b)) showed that HA stem protein was successfully attached to HBc VLPs.

Materials and Methods

Design and construction of hemagglutinin (HA) stem domain construct. To produce HA stem domain protein, the globular head domain (residues 60-291 in H3 numbering) of the A/California/05/2009 (H1N1) hemagglutinin (accession No. ACP41926) was replaced with a linker peptide (GSGSG). The signal peptide (residues 2-17), transmembrane domain (residues 521-554) and cytoplasmic tail (residues 555-566) of hemagglutinin were also deleted. The full HA sequence is provided as SEQ ID NO:1.

The sequence of the HA stem domain from influenza A virus A/California/05/2009 (H1N1) (accession No. ACP41926) was aligned to that of the HA stem domains from five other influenza A viruses, A/Viet Nam/1203/2004 (H5N1) (accession No. ABW90135), A/Hong Kong/1/1968 (H3N2) (accession No. AFG71887), A/Singapore/1/1957 (H2N2) (accession No. ACF54477), A/Puerto Rico/8/1934 (H1N1) (accession No. ACF41834), and A/South Carolina/1/1918(H1N1) (accession No. AAD17229). The sequences of HA stem domain from these 6 different variants were as follows (and also as shown in FIG. 1)

| Influenza A virus variants | Sequence of HA stem domain | Residues in H3 numbering |
|---|---|---|
| A/California/05/2009 (H1N1) (accession No. ACP41926) | SEQ ID NO: 2 | 18-59, 292-520 |
| A/Viet Nam/1203/2004(H5N1) (accession No. ABW90135) | SEQ ID NO: 3 | 17-58, 290-518 |
| A/Hong Kong/1/1968(H3N2) (accession No. AFG71887) | SEQ ID NO: 4 | 18-68, 293-521 |
| A/Singapore/1/1957(H2N2) (accession No. ACF54477) | SEQ ID NO: 5 | 16-57, 288-516 |
| A/Puerto Rico/8/1934(H1N1) (accession No. ACF41834) | SEQ ID NO: 6 | 18-59, 291-519 |
| A/South Carolina/1/1918(H1N1) (accession No. AAD17229) | SEQ ID NO: 7 | 18-59, 292-520 |

The HA stem domain construct of the invention was then modified to comprise a fusion between the HA stem domain, for example as set forth in SEQ ID NO:2-7, and a C-terminal 29 amino acid 'foldon' sequence. The foldon was used to trimerize the HA stem domain. The foldon domain is separated from the HA stem sequence by an optional cleavable TEV protease site and also contains an optional His$_6$ tag at the C-terminus. The DNA that codes for the construct was cloned into the pY71 vector using NdeI and SalI restriction sites. pY71 is a reduced size plasmid (1.76 kb) that utilizes the T7 promoter and contains a pUC19 origin of replication and a kanamycin resistance element (Kuchenreuther et al., 2009). The amino acid sequence expressed by the resulting construct is as follows in SEQ ID NO:8. The polynucleotide sequence encoding SEQ ID NO:8 is shown as SEQ ID NO:9.

Mutations of exposed hydrophobic residues. SEQ ID NO:2 was modified by targeted change to generate five different variants with different mutations of exposed hydrophobic residues were shown in the table as follows:

| Variants | Substitutions |
|---|---|
| Original (SEQ ID NO: 8) | |
| M1: SEQ ID NO: 10 | [I69T; I72E; I74T; C77T] |
| M2: SEQ ID NO: 11 | [I69T; I72E; I74T; C77T; F164D] |
| M3: SEQ ID NO: 12 | [I69T; I72E; I74T; C77T; F164D; L174D] |
| M4: SEQ ID NO: 13 | [F164D] |
| M5: SEQ ID NO: 14 | [F164D; L174D] |

Reduction of disulfide numbers. Based on mutant M5, two polypeptide regions (H38 to C43 and C49 to N61) containing hydrophobic residues and three cysteines were deleted, and cysteine 77 was mutated to threonine. The number of disulfide bonds in each monomer was thereby reduced from 4 to 2.

The sequences of stem polypeptides with 2 disulfide bonds is as follows:

| Variants | Sequences |
|---|---|
| M5: SEQ ID NO: 15 | [F164D; L174D] |
| M6: SEQ ID NO: 16 | ΔH38-C43, ΔC49-N61, C77T |

Cell-Free Protein Synthesis (CFPS). CFPS was conducted using the PANOx-SP (PEP, amino acids, nicotinamide adenine dinucleotide (NAD), oxalic acid, spermidine, and putrescine) cell-free system as described previously (Jewett and Swartz 2004) with several modifications. The standard PANOx-SP CFPS reaction mixture includes: 1.2 mM ATP, 0.85 mM each of GTP, UTP, and CTP, 33 mM phosphoenol pyruvate (Roche Molecular Biochemicals, Indianapolis, Ind.), 170 mM potassium glutamate, 10 mM ammonium glutamate, 16 mM magnesium glutamate, 1.5 mM spermidine, 1.0 mM putrescine, 0.17 mg/mL folinic acid, 13.3 μg/mL plasmid, approximately 100-300 μg/mL T7 RNA polymerase, 2 mM of each of the 20 unlabeled amino acids, 0.33 mM NAD, 0.26 mM Coenzyme A (CoA), 2.7 mM potassium oxalate, and 0.28 volumes of E. coli KC6 S30 extract (Goerke and Swartz 2008; Knapp et al. 2007). All reagents were obtained from Sigma-Aldrich (St. Louis, Mo.) unless otherwise noted.

Several modifications to PANOx SP CFPS were made to encourage disulfide bond formation. First, the cell extract was pretreated at room temperature for 1 h with 1 mM iodoacetamide (IAM). Prior to template DNA addition, a glutathione buffer (4 mM oxidized glutathione and 1 mM reduced glutathione, unless otherwise specified) was added to the cell-free reaction to stabilize the thiol/disulfide redox potential. Finally, DsbC, a periplasmic disulfide bond isomerase, was added to a final concentration of 100 μg/mL.

CFPS reactions to produce the antigen protein were conducted at 30° C. for 6 h. Small-scale CFPS reactions were carried out in 20 μL volumes in 1.5 mL microcentrifuge tubes. Preparative-scale reactions used 6 mL volumes with 1 mL per well in 6-well tissue culture plates (BD Falcon #3046, BD, Franklin Lakes, N.J.). 8.4 μM L-[U-$^{14}$C]-Leucine (PerkinElmer, Waltham, Mass.) was added to small-scale reactions and to 20 μL aliquots of preparative-scale reactions for measuring protein yields using a previously described trichloroacetic acid protocol (Calhoun and Swartz 2005) and a Beckman LS3801 liquid scintillation counter (Beckman Coulter, Fullerton, Calif.). The soluble fraction of preparative-scale reactions was recovered by centrifugation at 21,000×g, 15 min for further evaluation and purification.

Protein purification and refolding. After CFPS reaction, the insoluble inclusion bodies were washed and dissolved in denaturing buffer. The pure inclusion bodies were then purified and refolded. The buffer used in the dissolving, purification and refolding process, and the process flowcharts were shown as follows:

Procedure I (for Wild-Type and Mutants M1, M2, M3, M4, M5)
  Washing buffer I: 50 mM Tris-HCl; 100 mM NaCl; 1 mM EDTA; pH=8
  Washing buffer II: 100 mM $NaH_2PO_4$; 10 mM Tris-HCl; 20 mM Imidazole; pH=8
  Denaturing washing buffer: 8M Urea; 100 mM $NaH_2PO_4$; 10 mM Tris-HCl; 20 mM Imidazole; 1 mM DTT; pH=8
  Denaturing elution buffer: 8M Urea; 100 mM $NaH_2PO_4$; 10 mM Tris-HCl; 250 mM Imidazole; 1 mM DTT; pH=8
  Refolding buffer: 6→4→2M Urea; 50 mM Tris-HCl; 500 mM Arginine; GSSG/GSH (1:4 mM); 4 mM EDTA; pH=10.5
  Dialysis buffer: 50 mM Tris-HCl; 500 mM Arginine; GSSG/GSH (1:4 mM); 4 mM EDTA; pH=10.5
  Running buffer of HPLC: same as the dialysis buffer Procedure II (for Optimization of Protein Refolding Conditions by Orthogonal Experimental Design)
  Washing buffer I: 50 mM Tris-HCl; 100 mM NaCl; 1 mM EDTA; pH=8
  Washing buffer II: 100 mM $NaH_2PO_4$; 10 mM Tris-HCl; 20 mM Imidazole; pH=8
  Denaturing washing buffer: 8M Urea; 100 mM $NaH_2PO_4$; 10 mM Tris-HCl; 20 mM Imidazole; 1 mM DTT; pH=8
  Denaturing elution buffer: 8M Urea; 100 mM $NaH_2PO_4$; 10 mM Tris-HCl; 500 mM Imidazole; 1 mM DTT; pH=8
  Refolding buffer: 50 mM Tris or Histidine; Arginine (0 mM or 500 mM); NaCl (0 mM or 150 mM); Sucrose (0% or 10%); Glycerol (0% or 10%); Urea (0 mM or 0.5 mM); Brij35 (0% or 0.03%); 2 mM EDTA; CSSG/GSH (1:4 mM); pH=10.5
  Dialysis buffer: Refolding buffer without GSSG, GSH and EDTA
  Running buffer of HPLC: same as the dialysis buffer Procedure III (for Comparison of Detergent Brij 35 with Tween 20)
  Washing buffer I: 50 mM Tris-HCl; 100 mM NaCl; 1 mM EDTA; pH=8
  Washing buffer II: 100 mM $NaH_2PO_4$; 10 mM Tris-HCl; 20 mM Imidazole; pH=8
  Denaturing washing buffer: 8M Urea; 100 mM $NaH_2PO_4$; 10 mM Tris-HCl; 20 mM Imidazole; 1 mM DTT; pH=8
  Denaturing elution buffer: 8M Urea; 100 mM $NaH_2PO_4$; 10 mM Tris-HCl; 500 mM Imidazole; 1 mM DTT; pH=8
  Refolding buffer: 50 mM Tris-HCl; 600 mM Arginine; 2 mM EDTA; Cystamine/Cysteamine (0.5:5 mM); 0.05% Brij35 or 0.05% Tween 20; pH=8
  Dialysis buffer: 50 mM Tris-HCl; 100 mM Arginine; 0.05% Brij35 or 0.05% Tween 20; pH=8
  Running buffer of HPLC: same as the dialysis buffer Procedure IV (for Mutant M6)
  Washing buffer I: 50 mM Tris-HCl; 100 mM NaCl; 1 mM EDTA; pH=8
  Washing buffer II: 100 mM $NaH_2PO_4$; 10 mM Tris-HCl; 20 mM Imidazole; pH=8
  Denaturing washing buffer: 8M Urea; 100 mM $NaH_2PO_4$; 10 mM Tris-HCl; 20 mM Imidazole; 1 mM DTT; pH=8
  Denaturing elution buffer: 8M Urea; 100 mM $NaH_2PO_4$; 10 mM Tris-HCl; 500 mM Imidazole; 1 mM DTT; pH=8
  Denaturing buffer: 8M Urea; 50 mM Tris-HCl; 2 mM EDTA; 1 mM DTT; pH=8
  Refolding buffer: 50 mM Tris-HCl; 600 mM Arginine; 2 mM EDTA; Cystamine/Cysteamine (0.5:5 mM); 0.05% Brij35; pH=8
  Dialysis buffer: 50 mM Tris-HCl; 100 mM Arginine; 0.05% Brij35; pH=8

Size Exclusion HPLC. Refolded proteins were tested on a Ultrahydrogel 500 HPLC column, 300 mm×7.8 mm inner diameter with 10 μM particles (Waters). The running buffer was 50 mM Tris-HCl (pH 8.0), 500 mM Arginine, 0.05% Tween 20 or Brij 35, pumped at 0.3 mL/min. The sample injection volume was 80 μL. Protein absorbance was monitored in-line at 280 nm over a period of 60 min.

Constructs used for the assembly of HA stem domain construct and virus-like particle (VLP). To introduce sites for the incorporation of a non-natural amino acid (nnAA) with an alkyne group in the HA stem domain, a single TAG codon was introduced at three different locations (residues H173, D174 and G314) respectively, using QuikChange PCR (Stratagene, La Jolla, Calif.).

To incorporate nnAA with an azide group in Hepatitis B core (HBc) VLP, a methionine site was introduced at residue 76 for nnAA incorporation using QuikChange PCR. M66 was also replaced with a serine residue to avoid nnAA introduction at this site.

To facilitate nnAA incorporation into HA stem domain construct and HBc antigen respectively, 5 mM of p-propargyloxy-phenylalanine (PPF, with an alkyne group, MedChem Source LLP, Federal Way, Wash.) and 6 mM of azidohomoalanine (AHA, with an azide group, MedChem Source LLP, Federal Way, Wash.) were added to CFPS reactions respectively, in addition to 75-100 μg/mL of linearized plasmid harboring the orthogonal tRNA sequence (Cem Albayrak, Ph.D. thesis, 2012) and 250 μg/mL of the orthogonal tRNA synthetase (Patel and Swartz, 2011). PPF is the analog of tyrosine, and AHA is the analog of methionine. For global replacement of methionines, methionine was omitted from the CFPS reaction mixtures.

Azide-Alkyne click chemistry. The (3+2) cycloaddition click reactions were conducted in an anaerobic glovebox (Coy Laboratories, Grass Lake, Mich.) to preserve the reduced state of the tetrakis(acetonitrile)copper(I)hexafluorophosphate catalyst ([(CH3CN)4Cu]PF6 or simply Cu(I) catalyst) (Sigma Aldrich, St. Louis, Mo.). Cu(I) catalyst was added to reactions at 1 mM in addition to 0.5 mM of the enhancer ligand, tris(triazolylmethyl) amine (TTMA) (obtained from the Professor Christopher Chidsey Laboratory at Stanford University, Stanford, Calif.), to improve the rate of the click reactions. HBc VLP and HA stem domain construct were mixed with the Cu (I) catalyst and TTMA enhancer in 10 mM potassium phosphate (pH 8.0) with 0.01% Tween 20. Before addition of the Cu(I) catalyst, click reaction components were deoxygenated in 1.5 mL microcentrifuge tubes for 1 h in the anaerobic glovebox. The click reactions for attaching HBc VLP to HA stem domain construct were conducted for 2 h.

ELISA binding of HA stem constructs. In an enzyme-linked immunosorbent assay (ELISA), 50 µL of antibody C179 (Mouse IgG) (TAKAR Bio INC.) at 2 µg/mL concentrations were coated on 96-well ELISA plates (Microlon, flat-bottom, high binding; Greiner Bio One, Frickenhausen, Germany) and allowed to bind overnight at 4° C. Commercial HA consisted of amino acids 18-529 of the 2009 H1N1 strain (HA(ΔTM)(A/California/07/2009(H1N1); Immune Technology Corp., New York, N.Y.). Plates were then washed three times with wash buffer (PBS buffer with 0.1% Tween-20) and blocked with PBS buffer with 3% bovine serum albumin (blocking buffer) and placed at 37° C. for 1 h. After washing four times with wash buffer, 50 µL dilutions of 6 µg/mL commercial HA protein and refolded HA stem domain protein were then added to the plates and incubated at 37° C. for 1 h. Plates were again washed three times with wash buffer before adding 1 µg/mL of monoclonal anti-his biotin-conjugated antibody in blocking buffer and incubating at 37° C. for 1 h. Plates were again washed three times with wash buffer before adding peroxidase-conjugated anti-biotin antibody at a 1:1000 dilution in blocking buffer and incubating at 37° C. for 1 h. Plates were again washed six times before developing with 50 µL of TMB substrate (KPL) and quenching with 30 µL of 2% $H_2SO_4$. Each well was measured at $OD_{450}$ with an ELISA plate reader. Each data point indicates the mean of triplicate assay results and error bars represent standard deviation.

Example 2

The rapid dissemination of the 2009 pandemic H1N1 influenza virus emphasizes the need for universal influenza vaccines which would broadly protect against multiple mutated strains. Recent efforts have focused on the highly conserved hemagglutinin (HA) stem domain. Although the production of the HA stem domain as a possible universal influenza vaccine antigen has been attempted by several groups (Bommakanti et al. (2010) PNAS 107(31):13701-13706; Steel et al. (2010) Mbio 1(1); Wang et al. (2010) PNAS 107(44):18979-18984), this has proven to be technically challenging. The first challenge is that the HA stem domain has not evolved to fold and trimerize as an independent unit. Further, its contemporaneous folding along with that of the head domain most likely occurs co-translationally as first part of the stem, then the head, and finally the rest of the stem domain are extruded from the ER membrane and are orientated by this association. During this process, disulfide bonds must form within each monomer while avoiding inter-monomer linkage. Finally the absence of the head domain exposes internal HA polypeptides that may now be disordered, hydrophobic, or otherwise inappropriate as surface epitopes for stable and soluble protein.

Because of these complications, in vivo E. coli expression was low with yields of only 2 mg/l, and the HA stem polypeptides accumulated as inclusion bodies. Although some refolding methods have been attempted (Biesova et al. (2009) Vaccine 27(44):6234-6238; Curtis-Fisk et al. (2008) Protein Expression and Purification 61(2):212-219; Swalley et al. (2004) Biochemistry 43(19):5902-5911), the recovery yields of soluble products have been low, and properly folded stable trimeric assembly has not been confirmed.

Figure 14:
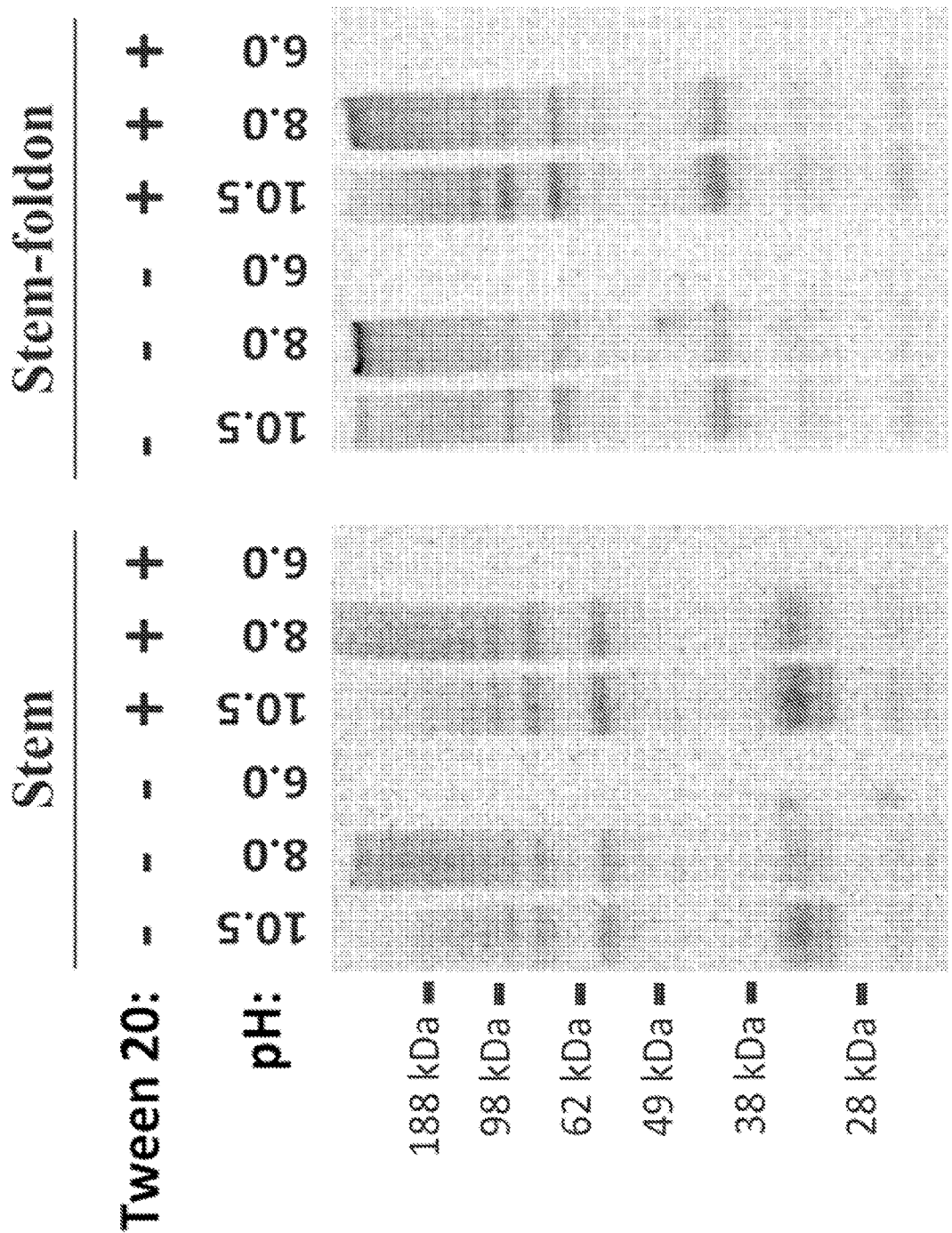
FIG. 14. Autoradiogram from non-reducing SDS-PAGE gel of refolded proteins. Proteins were refolded under different conditions: different pH environments (pH 6.0, pH 8.0, pH 10.5), with (+) or without (−) 0.05% (w/v) Tween 20. The foldon sequence was fused to the C-terminus of the stem domain to induce trimerization.
Figure 15:
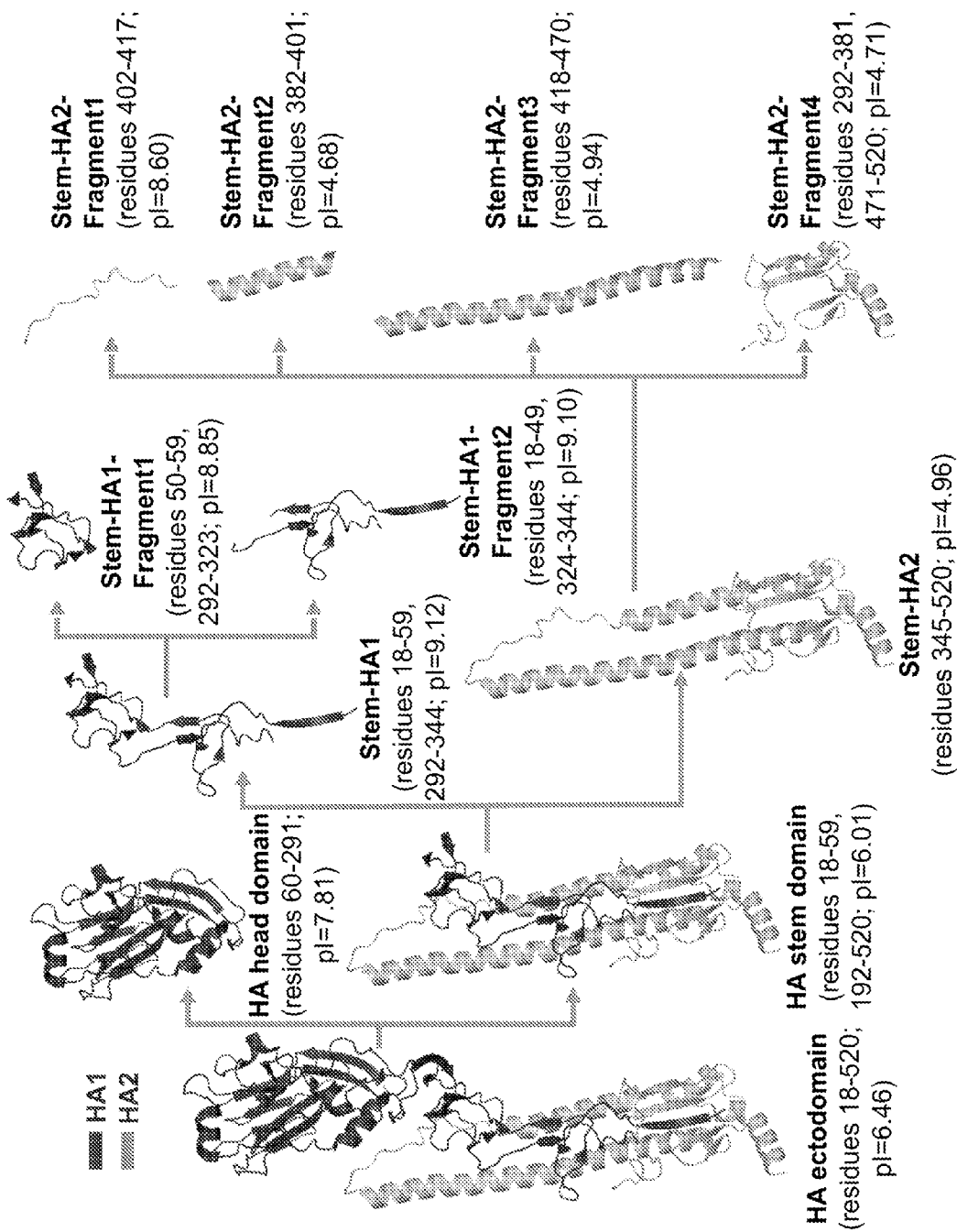
FIG. 15. Isoelectric point (pi) analysis of HA protein fragments. The HA ectodomain from the influenza virus A/California/05/2009 (H1N1) (accession No. ACP41926) was chosen as the target. All the residue numbers were in H3 numbering.
Figure 16:
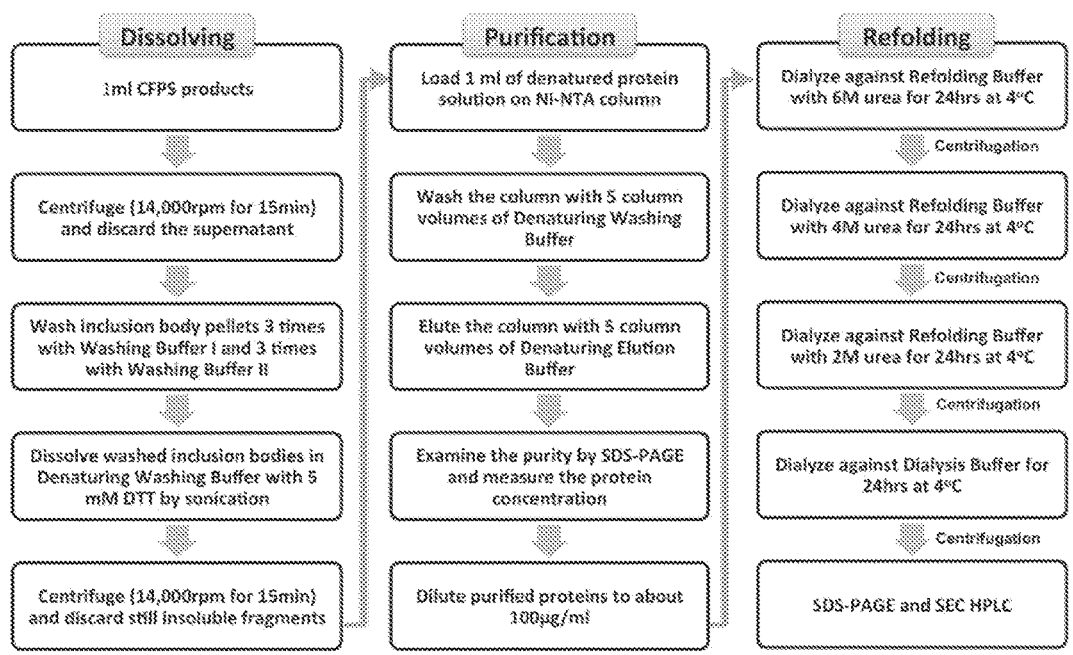
FIG. 16. Procedure I (for wild-type and mutants M1, M2, M3, M4, M5).
Figure 17:
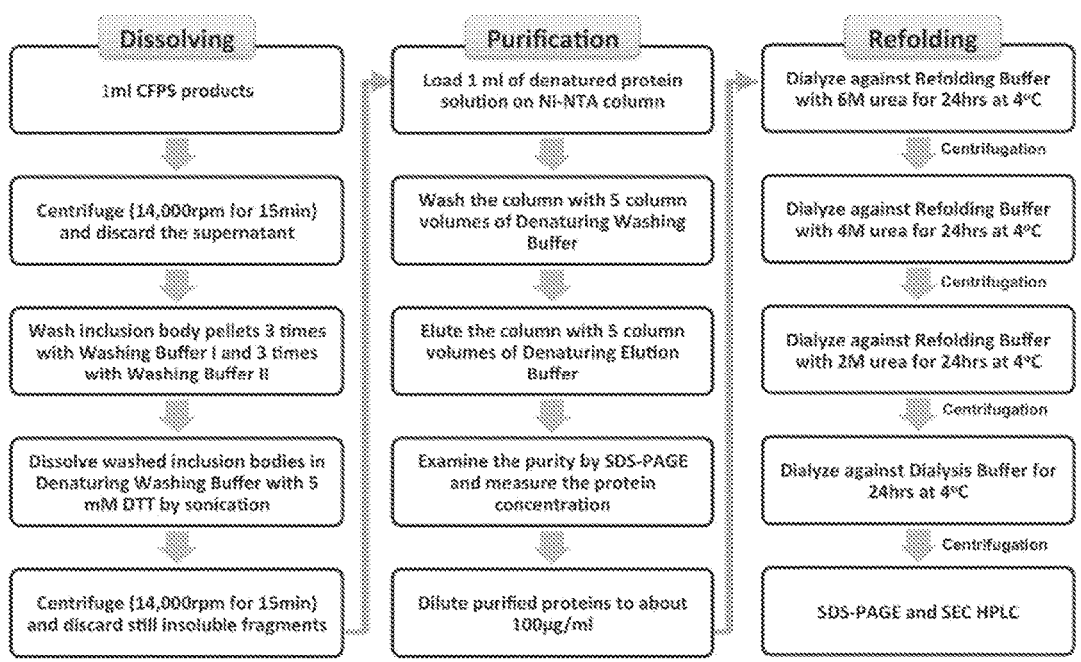
FIG. 17. Procedure II (for optimization of protein refolding conditions by orthogonal experimental design).
Figure 18:
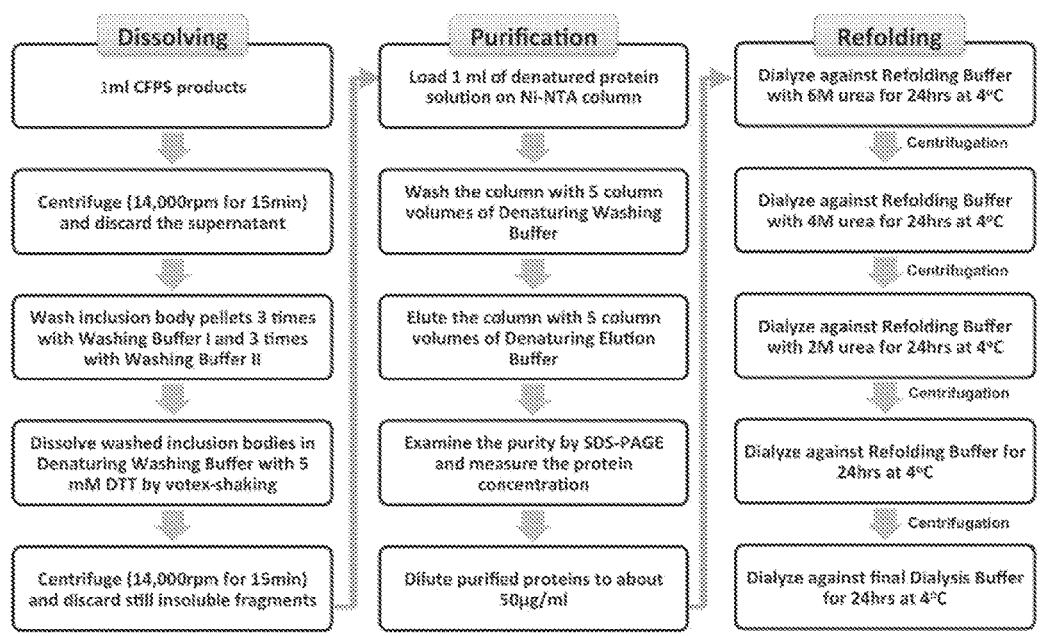
FIG. 18. Procedure III (for comparison of detergent Brij 35 with Tween 20).

Refolding of the inclusion bodies was attempted under different pH conditions. Eight molar urea was used to solubilize the inclusion bodies. Oxidized (GSSG) and reduced glutathione (GSH) (molar ratio 1:4) were added to establish a sulfhydryl/disulfide redox environment for the formation and potential isomerization of correct disulfide bonds. L-arginine (0.5 M) and the detergent, Tween 20, were also added to assist in refolding. Three different pH values (6.0, 8.0 and 10.5) were tested with results shown in FIG. 14. At pH 6.0, most of the protein was lost, apparently adhering to the dialysis membrane. At pH 8.0, most reaggregated, while at pH 10.5, less aggregation occured. However, the soluble fraction from the pH 10.5 procedure also aggregated when the pH was reduced to 8.0. This prompted us to examine regional pI values for the polypeptide calculated using the program, ProtParam (FIG. 15). The theoretical pI values of Stem-HA1-Fragment1 (pI 8.85), Stem-HA1-Fragment2 (pI 9.10) and Stem-HA2-Fragment1 (pI 8.60) were above 8.5, while the pI values of other stem domain fragments were below 5. This suggested the potential for significant intermolecular ionic attractions at neutral pH, which would largely be avoided at pH 10.5. Furthermore, since the detergent, Tween 20, reduced aggregation, inappropriate hydrophobic interactions were also suggested.

Based on these considerations, five sets of mutations were designed (FIG. 4) to either mitigate newly exposed hydrophobicity, reduce the potential for intermolecular ion pairing or both. Five different groups of mutations were evaluated, M1 (I69T+I72E+I74T+C77T), M2 (I69T+I72E+I74T+C77T+F164D), M3 (I69T+I72E+I74T+C77T+F164D+L174D), M4 (F164D) and M5 (F164D+L174D). Table 3 indicates the effects of the mutations on the pIs of two newly exposed stem domain fragments (Stem-HA1-Fragment1 and Stem-HA2-Fragment1). It should be noted that the targeted mutations were distant from the surface recognized by the broadly neutralizing antibody. By the evaluation using size-exclusion HPLC (FIG. 5), the M1 group of mutations (I69T+I72E+I74T+C77T) did not appear to reduce aggregation, but mutants M3 and M5 produced much fewer aggregates than the wild-type or other variants. The most influential mutations appeared to be F164D+L174D. Therefore, the mutant M5 (F164D+L174D) was used for further development. Note that these changes reduced both the hydrophobicity and the pI (by introducing two negative charges) of the newly exposed protein surface.

To avoid the formation of undesired intermolecular S—S bonds and to further reduce surface hydrophobicity and lysine residues (thereby reducing the pI of these regions), and also to avoid regions with possibly disordered structure, mutant M5 was further modified by deleting two polypeptide regions (H38 to C43 and C49 to N61) containing hydrophobic residues, two positively charged lysines and three cysteines. Cysteine 77 was also mutated to threonine to remove an unpaired cysteine (FIG. 7). Again, the deleted regions are far away from the neutralizing antibody binding region. The number of disulfide bonds in each monomer was thereby decreased from 4 to 2. The new mutant was named M6. SDS-PAGE results (FIG. 7) showed that these modifications greatly decreased the formation of undesired intermolecular disulfide bonds.

What is claimed is:

1. A fusion protein, comprising
an influenza hemagglutinin (HA) stem antigen where HA globular head domain, residues 60-291 in H3 numbering is replaced with a linker peptide, signal peptide residues 2-17, transmembrane domain residues 521-554 and cytoplasmic tail residues 555-566 are deleted, where amino acid numbering is made relative to SEQ ID NO:1, wherein the fusion protein comprises not more than two disulfide bonds, and which HA stem domain is modified by (a) substitution of at least one hydrophobic amino acid with at least one polar amino acid, (b) deletion of regions in the stem containing hydrophobic residues and cysteines; (c) fusion to a foldon trimerization domain.

2. The fusion protein of claim 1 wherein the at least one hydrophobic amino acid is selected from I69, I72, I74, C77, F164, and L174.

3. The fusion protein of claim 1, comprising at least one unnatural amino acid at a defined position in the middle of the HA stem domain.

4. The fusion protein of claim 1, wherein the unnatural amino acid is linked to a virus like particle.

5. The fusion protein of claim 1, further comprising an exogenous motif for protease cleavage.

6. The fusion protein of claim 1, further comprising a tag for purification.

7. An isolated polypeptide comprising an amino acid sequence selected from SEQ ID NO:8, 10, 11, 12, 13, 14, 15 and 16.

8. The isolated polypeptide of claim 7, further comprising an unnatural amino acid in the middle of the HA stem domain.

9. An isolated polypeptide comprising an HA stem domain of SEQ ID NO:2, 3, 4, 5, 6 and 7, where HA globular head domain, residues 60-291 in H3 numbering is replaced with a linker peptide, signal peptide residues 2-17, transmembrane domain residues 521-554 and cytoplasmic tail residues 555-566 are deleted, where amino acid numbering is made relative to SEQ ID NO:1, fused to a C-terminal foldon sequence.

10. The isolated polypeptide of claim 8, comprising a set of amino acid modifications selected from (I69T, I72E, I74T, C77T); (I69T, I72E, I74T, C77T, F164D); (I69T, I72E, I74T, C77T, F164D, L174D); (F164D) and (F164D, L174D).

11. The isolated polypeptide of claim 9, further comprising amino acid modifications selected from (F164D, L174D); and (ΔH38-C43, ΔC49-N61, C77T).

12. The isolated polypeptide of claim 9, further comprising an unnatural amino acid in the middle of the HA stem domain.

* * * * *